United States Patent
Knappe et al.

(10) Patent No.: US 8,398,960 B2
(45) Date of Patent: Mar. 19, 2013

(54) STYLING AGENTS GIVING A HIGH DEGREE OF HOLD IN HUMID CONDITIONS

(75) Inventors: Thorsten Knappe, Schenefeld (DE); Rene Scheffler, Ellerau (DE)

(73) Assignee: Henkel AG & Co. KGaA (DE)

( * ) Notice: Subject to any disclaimer, the term of this patent is extended or adjusted under 35 U.S.C. 154(b) by 193 days.

(21) Appl. No.: 12/775,528

(22) Filed: May 7, 2010

(65) Prior Publication Data
US 2010/0215609 A1    Aug. 26, 2010

Related U.S. Application Data

(63) Continuation of application No. PCT/EP2008/063711, filed on Oct. 13, 2008.

(30) Foreign Application Priority Data

Nov. 9, 2007  (DE) .......................... 10 2007 053 951

(51) Int. Cl.
| | |
|---|---|
| *A61K 8/00* | (2006.01) |
| *A61K 8/58* | (2006.01) |
| *A61K 8/65* | (2006.01) |
| *A61Q 5/06* | (2006.01) |
| *A61Q 5/12* | (2006.01) |
| *A45D 7/04* | (2006.01) |

(52) U.S. Cl. ................. 424/70.1; 424/70.11; 424/70.12; 424/70.13; 424/70.14; 424/70.15; 132/203

(58) Field of Classification Search .......................... None
See application file for complete search history.

(56) References Cited

U.S. PATENT DOCUMENTS

| 3,753,968 | A | 8/1973 | Ward |
| 5,773,595 | A | 6/1998 | Weuthen et al. |
| 6,235,913 | B1 | 5/2001 | Raths et al. |
| 7,332,466 | B2 | 2/2008 | Schmid et al. |
| 2001/0018046 | A1* | 8/2001 | Vitale et al. ................. 424/70.16 |
| 2005/0281774 | A1* | 12/2005 | Muller et al. .............. 424/70.15 |

FOREIGN PATENT DOCUMENTS

| DE | 19523596 A1 | 1/1997 |
| DE | 19756454 C1 | 6/1999 |
| EP | 0671161 A1 | 9/1995 |
| EP | 1302191 A2 | 4/2003 |
| EP | 1502577 A2 | 2/2005 |
| EP | 1712256 A1 | 10/2006 |

OTHER PUBLICATIONS

Hair Styling Ingredients, "Hair Styling Ingredients", 2002, accessed from: http://www.thefreelibrary.com/Hair+styling+ingredients.-a088824035, pp. 1-10.*

Luviquat Polymer Grades. MEMC050202e-04, (2005), pp. 1-32.
International Cosmetic Ingredient Dictionary and Handbook. The Cosmetic Toiletry, and Fragrance Association, 7th edition, (1997).
Römp-Lexikon Chemie. Georg Thieme Verlag, vol. 10, (1997), p. 1764.

* cited by examiner

*Primary Examiner* — Michael G Hartley
*Assistant Examiner* — Lance Rider
(74) *Attorney, Agent, or Firm* — Ingrassia Fisher & Lorenz, P.C.

(57) ABSTRACT

The invention relates to agents for temporarily shaping keratin fibers, said agents giving a very high degree of hold without impairing its flexibility and humidity resistance. The agents according to the invention contain, in a cosmetically acceptable carrier, a) at least one copolymer A which contains at least one structural entity of formula (I)—

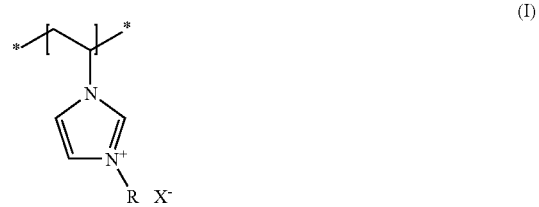

(I)

wherein R is a $C_1$-$C_{30}$ alkyl group, a $C_1$-$C_4$ aralkyl group, a $C_2$-$C_6$ alkenyl group or a $C_2$-$C_6$ hydroxyalkyl group and $X^-$ is a physiologically acceptable anion, and which contains at least one further structural entity of formula (II)—

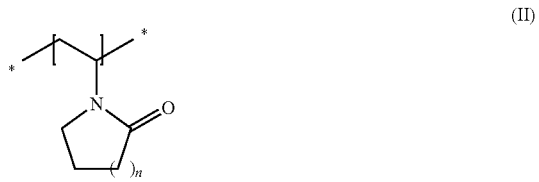

(II)

wherein n is 1, 2 or 3 as the number of methylene entities; b) and at least one acrylate polymer B, which is different from copolymer A, selected from b1) polyacrylic acid and/or b2) copolymers of methacrylic acid with acrylamidopropane sulfonic acid and/or b3) copolymers of acrylic acid with methacrylic acid and acrylic esters and/or b4) copolymers of acrylic acid with methacrylic acid with acrylic esters and methacrylic esters and/or b5) copolymers of acrylic esters with methacrylic acid.

11 Claims, No Drawings

STYLING AGENTS GIVING A HIGH DEGREE OF HOLD IN HUMID CONDITIONS

CROSS REFERENCE TO RELATED APPLICATIONS

The present application is a continuation of International Application No. PCT/EP2008/063711 filed 13 Oct. 2008, which claim priority to German Patent Application No. 10 2007 053 951.9 filed 9 Nov. 2007.

The present invention relates to agents for temporarily shaping keratin-containing fibers comprising a specific combination of polymers, to the use of said agents for temporarily shaping keratinic fibers and to aerosol hair foams based on said agents.

Keratin-containing fibers are understood to include all animal hair (e.g., wool, horsehair, angora hair, furs, and feathers) and products or fabrics produced from them. However, keratin-containing fibers preferably concern human hair.

Today, a suitably looking hairstyle is generally desired as an essential part of a well-groomed appearance. Based on actual fashion trends, time and again hairstyles are considered chic, which, for many types of hair, can only be formed or sustained over a longer period of up to several days by the use of certain consolidating materials. Thus, hair treatments, which can provide a permanent or temporary hairstyling, play an important role. Temporary styling intended to provide a good hold without compromising the healthy appearance of hair (such as its gloss) can be obtained, for example, by use of hairsprays, hair waxes, hair gels, hair foams, setting lotions, etc.

Suitable agents for temporary hairstyling usually include synthetic polymers as the styling component. Preparations comprising a dissolved or dispersed polymer can be applied on hair by propellants or by a pumping mechanism. Other preparations such as hair gels and hair waxes are not generally applied directly on the hair, but rather dispersed with a comb or by hand.

An important property of an agent for temporary styling of keratin fibers, also referred to as styling agents, involves giving the treated fibers the strongest possible hold for the shape created. If the keratin fibers concern human hair, then one also speaks of a strong hairstyle hold or a high degree of hold of the styling agent. Styling hold is affected by the type and quantity of synthetic polymer used, but there can also be an influence from other components in the styling agent.

In addition to a high degree of hold, styling agents must fulfill a whole series of additional requirements. These requirements can be broadly subdivided into properties on the hair, properties of the formulation in question (e.g., properties of the foam, gel or aerosol spray), and properties regarding the handling of the styling agent, wherein particular importance is attached to the properties on the hair. These include moisture resistance, low stickiness and a balanced conditioning effect. Furthermore, a styling agent should be universally applicable for as many types of hair as possible.

To do meet these multiple requirements, various synthetic polymers have been developed and are being used in styling agents. These polymers can be subdivided into cationic, anionic, non-ionic and amphoteric film-forming and/or setting polymers. Ideally, these polymers form a polymer film when applied to hair, imparting a strong hold to the hairstyle while also being sufficiently flexible so as to not break under stress. If the polymer film is too brittle, so-called film plaques develop (i.e., residues that are shed with movement of the hair and give the impression that the user of the respective styling agent has dandruff).

To develop styling agents that in combination have all the desired properties still presents problems. This is true in particular of styling agents that are intended to have an especially strong hold.

Accordingly, the present invention is directed towards an agent for temporary styling of keratin fibers that has a very high degree of hold without impairing flexibility and good resistance to humidity.

It has now been surprisingly found that this can be achieved by a combination of specific polymers.

Accordingly, a first subject matter of the present invention is a cosmetic agent that comprises, in an acceptable carrier—
a) at least one copolymer A having at least one structural unit according to Formula (I)

wherein R is a $C_1$ to $C_{30}$ alkyl group, a $C_1$ to $C_4$ aralkyl group, a $C_2$ to $C_6$ alkenyl group or a $C_2$ to $C_6$ hydroxyalkyl group; and $X^-$ is a physiologically compatible anion; and further having at least one structural unit according to Formula (II)

wherein n is 1, 2 or 3 as the number of methylene units; and
b) at least one acrylate polymer B different from copolymer A and chosen from
b1) polyacrylic acid, and/or
b2) copolymers of methacrylic acid with acrylamido propane sulfonic acid, and/or
b3) copolymers of acrylic acid with methacrylic acid and acrylic acid esters, and/or
b4) copolymers of acrylic acid with methacrylic acid with acrylic acid esters and methacrylic acid esters, and/or
b5) copolymers of acrylic acid esters with methacrylic acid.

Film-forming and/or setting copolymers A are known. The same is true for acrylate polymers B and their use as film-forming and/or setting polymers. It has now been surprisingly found that an appropriate combination of both polymer types exhibits self-thickening properties, wherein the excellent film-forming and/or setting properties of the individual polymers are augmented. Styling agents comprising a combination of these polymers provide a synergistic increase in the degree of hold and good moisture resistance of the obtained hold, without impairing their ability to be washed out.

Cosmetics according to the invention comprise at least one copolymer A as the first mandatory ingredient. This copolymer possesses at least one structural unit according to Formula (I) and at least one structural unit according to Formula (II) and moreover can have further structural units that can be polymerized in by adding suitable monomers during polymerization.

In Formula (I) R is a $C_1$ to $C_{30}$ alkyl group, a $C_1$ to $C_4$ aralkyl group, a $C_2$ to $C_6$ alkenyl group or a $C_2$ to $C_6$ hydroxyalkyl group. Preferred R groups include —$CH_3$, —$CH_2CH_3$, —$CH_2CH_2CH_3$, $CH(CH_3)_2$, —$(CH_2)_3CH_3$, —$CH_2$—CH$(CH_3)_2$, —$CH(CH_3)CH_2CH_3$, —$C(CH_3)_3$, —$CH_2OH$, —$CH_2CH_2OH$, —$CH_2CH_2CH_2OH$, —$CH(OH)CH_2CH_3$, and —$CH_2CH(OH)CH_3$.

$X^-$ is a physiologically compatible anion, with preferred anions being chloride, bromide, iodide, sulfate, methosulfate, ethyl sulfate, tosylate and tetrafluoroborate.

In Formula (II), n is the number of methylene groups. When n=1, Formula (II) is a vinyl pyrrolidone unit; when n=2, a vinyl piperidinone unit; and when n=3, a vinyl caprolactam unit.

Particularly preferred inventive agents comprise a copolymer A1 as the copolymer A, wherein copolymer A1 comprises— at least one structural unit according to Formula (I)

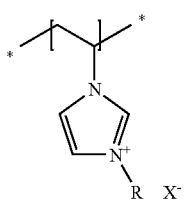

(I)

wherein R is a methyl group and X is methosulfate, and
at least one further structural unit according to Formula (II)

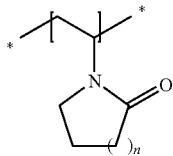

(II)

wherein n is 1 methylene unit.

Quite particularly preferred copolymers A1 comprise 10 to 30 mol %, preferably 15 to 25 mol % and particularly 20 mol % of structural units according to Formula (I), and 70 to 90 mol %, preferably 75 to 85 mol % and particularly 80 mol % of structural units according to Formula (II).

It is particularly preferred when copolymers A1 comprise, in addition to polymer units resulting from incorporation of the cited structural units according to Formula (I) and (II) into the copolymer, a maximum of 5 wt. %, preferably a maximum of 1 wt. % of polymer units that trace back to the incorporation of other monomers. Copolymers A1 are preferably exclusively formed from structural units of Formula (I) and (II) can be described by the general Formula—

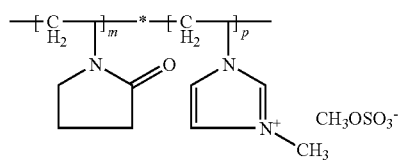

wherein each of the indices m and n vary according to the molar mass of the polymer and are not intended to portray block copolymers. In fact, structural units of Formula (I) and Formula (II) can be statistically distributed in the molecule According to INCI nomenclature, N-methyl vinyl imidazole/vinyl pyrrolidone copolymers are called POLYQUATERNIUM-44 and are available, for example, from BASF under the trade name Luviquat® UltraCare.

Particularly preferred inventive agents comprise a copolymer A1 having molar masses within a defined range. Inventive agents are preferred in which the molar mass of the copolymer A1 is from 50 to 400 kDa, preferably from 100 to 300 kDa, more preferably from 150 to 250 kDa and particularly from 190 to 210 kDa.

In addition to or instead of copolymer(s) A1, the inventive agents can also comprise copolymers A2 that possess structural units of Formula (II) as the additional structural units, wherein n is the number 3.

Further particularly preferred inventive agents comprise a copolymer A2 as the copolymer A, said copolymer A2 comprising— at least one structural unit according to Formula (I)

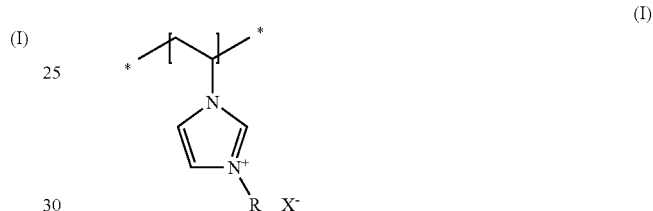

(I)

wherein R is a methyl group and X is methosulfate,
at least one further structural unit according to Formula (II)

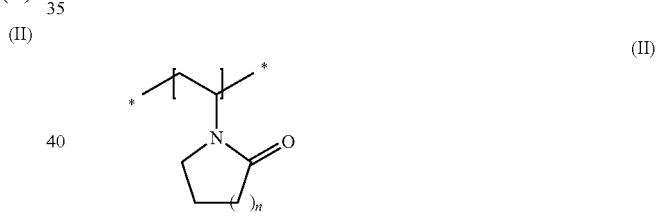

(II)

wherein n is 1 methylene unit,
at least one further structural unit according to Formula (II)

(II)

wherein n is 3 methylene units.

It is also particularly preferred when the copolymers A2 comprise, in addition to polymer units that result from the incorporation of the cited structural units in accordance with Formula (I) and (II) into the copolymer, a maximum of 5 wt. %, preferably a maximum of 1 wt. % of polymer units that trace back to the incorporation of other monomers. Copolymers A2 are preferably exclusively formed from structural units Formula (I) and (II) and can be described by the general Formula—

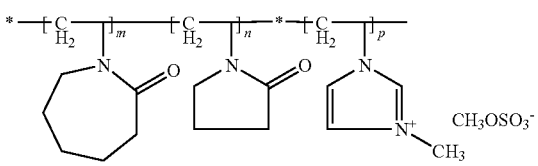

wherein each of the indices m, n and p vary according to the molar mass of the polymer and are not intended to portray block copolymers. In fact, structural units of Formula (I) and Formula (II) can be statistically distributed in the molecule.

According to INCI nomenclature, N-methyl vinyl imidazole/vinyl pyrrolidone/vinyl caprolactam copolymers are called POLYQUATERNIUM-46 and are available, for example, from BASF under the trade name Luviquat® Hold.

Quite particularly preferred copolymers A2 comprise 1 to 20 mol %, preferably 5 to 15 mol % and particularly 10 mol % of structural units according to Formula (I) and 30 to 50 mol %, preferably 35 to 45 mol % and particularly 40 mol % of structural units according to Formula (II) with n=1, and 40 to 60 mol %, preferably 45 to 55 mol % and particularly 60 mol % of structural units according to Formula (II) with n=3.

Particularly preferred inventive agents comprise a copolymer A2 having molar masses within a defined range. Here, inventive agents are preferred, in which the molar mass of the copolymer A2 is from 100 to 1000 kDa, preferably from 250 to 900 kDa, more preferably from 500 to 850 kDa and particularly from 650 to 710 kDa.

In addition to or instead of copolymer(s) A1 and/or A2, the inventive agents can also comprise copolymers A3 having structural units of Formula (II) as additional structural units wherein n is the number 3, as well as additional di-structural units from vinyl imidazole units and additional structural units from acrylamide and/or methacrylamide units.

Further particularly preferred inventive agents comprise a copolymer A3 as copolymer A, said copolymer A3 comprising at least one structural unit according to Formula (I)—

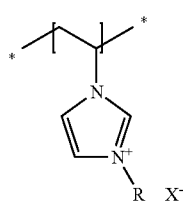

(I)

wherein R is a methyl group and X is methosulfate, at least one further structural unit according to Formula (II)—

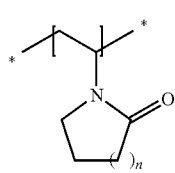

(II)

wherein n is 1 methylene unit, at least one further structural unit according to Formula (III)—

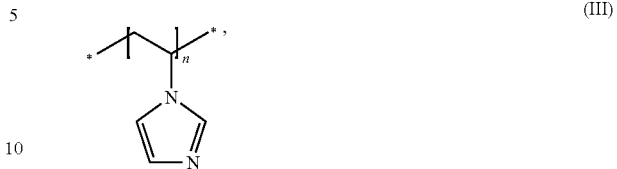

(III)

and at least one further structural unit according to Formula (IV)—

(IV)

It is also particularly preferred when copolymers A3 comprise, in addition to polymer units that result from the incorporation of the cited structural units in accordance with Formula (I), (II), (III) and (IV) into the copolymer, a maximum of 5 wt. %, preferably a maximum of 1 wt. % of polymer units that trace back to the incorporation of other monomers. Copolymers A3 are preferably exclusively formed from structural units of Formula (I), (II), (III) and (IV) and can be described by the general Formula

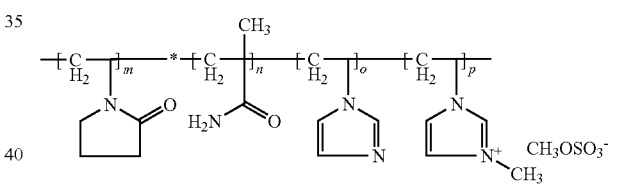

wherein each of the indices m, n, o and p vary according to the molar mass of the polymer and are not intended to portray block copolymers. In fact, structural units of Formula (I), (II), (III) and Formula (IV) can be statistically distributed in the molecule.

According to INCI nomenclature, N-methyl vinyl imidazole/vinyl pyrrolidone/vinyl imidazole/methacrylamide copolymers are called POLYQUATERNIUM-68 and are available for example from BASF under the trade name Luviquat® Supreme.

Quite particularly preferred copolymers A3 comprise 1 to 12 mol %, preferably 3 to 9 mol % and particularly 6 mol % of structural units according to Formula (I), and 45 to 65 mol %, preferably 50 to 60 mol % and particularly 55 mol % of structural units according to Formula (II) with n=1, 1 to 20 mol %, preferably 5 to 15 mol % and particularly 10 mol % of structural units according to Formula (III), and 20 to 40 mol %, preferably 25 to 35 mol % and particularly 29 mol % of structural units in accordance with Formula (IV).

Particularly preferred inventive agents comprise a copolymer A3 having molar masses within a defined range. Here, inventive agents are preferred in which the molar mass of the copolymer A3 is from 100 to 500 kDa, preferably from 150 to 400 kDa, more preferably from 250 to 350 kDa and particularly from 290 to 310 kDa.

Regardless of whether only one copolymer A or a plurality of copolymers A are employed and independently of the choice of the specific copolymer A, inventive agents are preferred, in which the total quantity of copolymers A, based on the weight of the ready for use agent, is 0.05 wt. % to 5 wt. %, preferably 0.1 to 4 wt. % and particularly 0.25 to 3 wt. %.

Inventive agents comprise at least one additional polymer B from the acrylate polymers (i.e., polymers having at least one monomer unit from acrylic acid and/or methacrylic acid and/or their esters). This acrylate polymer is selected from—
- b1) polyacrylic acid, and/or
- b2) copolymers of methacrylic acid with acrylamido propane sulfonic acid, and/or
- b3) copolymers of acrylic acid with methacrylic acid and acrylic acid esters, and/or
- b4) copolymers of acrylic acid with methacrylic acid with acrylic acid esters and methacrylic acid esters, and/or
- b5) copolymers of acrylic acid esters with methacrylic acid.

Thus for example, preferred inventive agents comprise polyacrylic acid as polymer B. This possesses structural units of the Formula—

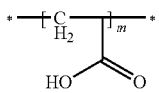

wherein m varies according to molar mass.

Particularly preferred inventive agents comprise polyacrylic acids as polymer b1, said polyacrylic acids having a molar mass of 10 to 250 kDa, preferably from 25 to 200 kDa, more preferably from 50 to 150 kDa and particularly from 70 to 100 kDa.

Polymers b1 are preferably employed within specific quantitative ranges. Here, preferred inventive agents comprise, based on total weight of the ready-for-use agent, 0.05 to 5 wt. %, preferably 0.1 to 4 wt. % and particularly 0.25 to 3 wt. % of polymer(s) b1.

In addition to or instead of polymer(s) b1, inventive agents can also comprise copolymers b2 from copolymers of methacrylic acid with acrylamido propane sulfonic acid.

These can be described by the general Formula—

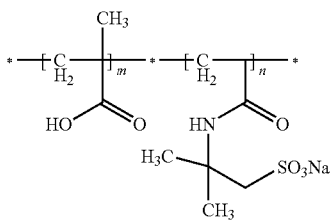

wherein each of the indices m and n vary according to the molar mass of the polymer and are not intended to portray block copolymers. In fact, structural units can be statistically distributed in the molecule.

Particularly preferred inventive agents comprise copolymers of methacrylic acids with acrylamido propane sulfonic acid as copolymer b2, said copolymers having a molar mass of 100 to 2500 kDa, preferably from 250 to 2000 kDa, more preferably from 500 to 1750 kDa and particularly from 800 to 1500 kDa.

Copolymers b2 are preferably employed within specific quantitative ranges. Here, preferred inventive agents comprise, based on the weight of the ready for use agent, 0.05 to 5 wt. %, preferably 0.1 to 4 wt. % and particularly 0.25 to 3 wt. % of copolymer(s) b2.

Copolymers of methacrylic acid with acrylamido propane sulfonic acid are available, for example, under the trade name Fixomer® A-30 (Nalco).

In addition to or instead of polymer(s) b1 and/or copolymer(s) b2, inventive agents can also comprise copolymers b3 from copolymers of acrylic acid with methacrylic acid and acrylic acid esters.

These can be described by the general Formula—

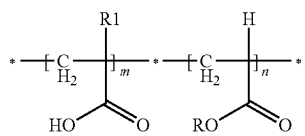

wherein each of the indices m and n vary according to the molar mass of the polymer and are not intended to portray block copolymers. In fact, structural units can be statistically distributed in the molecule. R1 stands for H or $CH_3$.

Particularly preferred inventive agents comprise copolymers of acrylic acid with methacrylic acids and acrylic acid esters as the copolymer b3, said copolymers having a molar mass of 50 to 500 kDa, preferably from 100 to 400 kDa, more preferably from 150 to 300 kDa and particularly from 200 to 250 kDa.

Copolymers b3 are preferably employed within specific quantitative ranges. Here, preferred inventive agents comprise, based on total weight of the ready-for-use agent, 0.05 to 5 wt. %, preferably 0.1 to 4 wt. % and particularly 0.25 to 3 wt. % of copolymer(s) b3.

A particularly preferred copolymer b3 is named according to the INCI nomenclature as Acrylates Copolymer. This type of polymer is available, for example, under the trade name Aculyn® 33A (Rohm & Haas).

In addition to or instead of the polymer(s) b1 and/or the copolymer(s) b2 and/or the copolymer(s) b3, inventive agents can also comprise polymers b4 from copolymers of acrylic acid with methacrylic acid and ethoxylated acrylic acid esters and ethoxylated methacrylic acid esters. Preferred polymers b4 are chosen from at least one compound from polymers b4-1 and b4-2 that are described in more detail below. The inventive agent particularly preferably comprises at least one polymer b4-2 as the polymer b4.

Preferred inventive agents comprise copolymers of acrylic acid with methacrylic acids and ethoxylated acrylic acid esters and ethoxylated methacrylic acid esters as the copolymer b4, said copolymers having a molar mass of 100 to 500 kDa, preferably from 150 to 400 kDa, more preferably from 200 to 300 kDa and particularly from 225 to 275 kDa.

The copolymers b4 are preferably employed within specific quantitative ranges. Here, preferred inventive agents comprise, based on total weight of the ready-for-use agent, 0.05 to 5 wt. %, preferably 0.1 to 4 wt. % and particularly 0.25 to 3 wt. % of copolymer(s) b4.

Polymers b4-1 can be described by the general Formula (b4-1)—

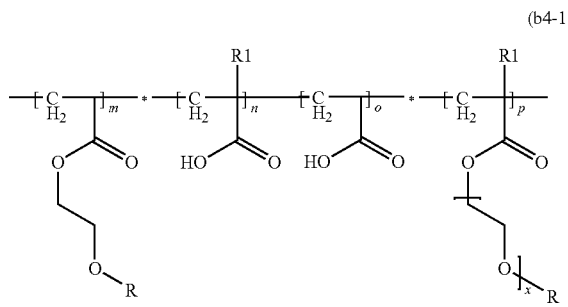

(b4-1)

wherein each of the indices m, n, o and p vary according to the molar mass of the polymer and are not intended to portray block copolymers. In fact, structural units can be statistically distributed in the molecule. R1 is a methyl group, R is a hydrocarbon group containing 1 to 22 carbon atoms, and x is 0 to 50.

Particularly preferred copolymers b4-1 possess 20 to 30 EO units (x=20, 21, 22, 23, 24, 25, 26, 27, 28, 29, 30) and possess a stearyl group or behenyl group as the R group.

Particularly preferred polymers b4-2 can be described by the general Formula (b4-2)—

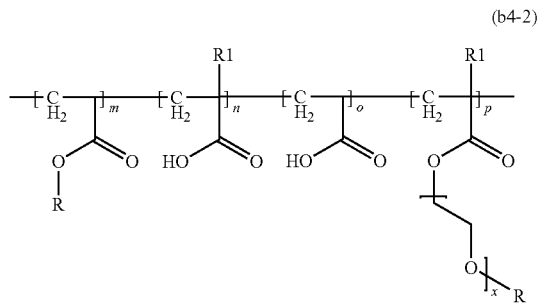

(b4-2)

wherein each of the indices m, n, o and p vary according to the molar mass of the polymer and are not intended to portray block copolymers. In fact, structural units can be statistically distributed in the molecule. R1 is a methyl group, R is a hydrocarbon group containing 1 to 22 carbon atoms, and x is 1 to 50.

Particularly preferred inventive agents comprise copolymers of acrylic acid with methacrylic acids and ethoxylated acrylic acid esters and ethoxylated methacrylic acid esters as the copolymer b4-2, said copolymers having a molar mass of 100 to 500 kDa, preferably from 150 to 400 kDa, more preferably from 200 to 300 kDa and particularly from 225 to 275 kDa.

Copolymers b4-2 are preferably employed within specific quantitative ranges. Here preferred inventive agents comprise, based on weight of the ready-for-use agent, 0.05 to 5 wt. %, preferably 0.1 to 4 wt. % and particularly 0.25 to 3 wt. % of copolymer(s) b4-2.

Particularly preferred copolymers b4-2 possess 20 to 30 EO units (x=20, 21, 22, 23, 24, 25, 26, 27, 28, 29, 30) and possess a stearyl group or behenyl group as the R group.

A more particularly preferred copolymer b4-2 possesses 25 EO units, is esterified with behenyl alcohol, and is named according to the INCI nomenclature as Acrylates/Beheneth-25 Methacrylate Copolymer. A polymer of this type is available, for example, under the trade name Aculyn® 28 (Rohm & Haas).

In addition to or instead of the polymer(s) b1 and/or the copolymer(s) b2 and/or the copolymer(s) b3 and/or the copolymer(s) b4, inventive agents can also comprise polymers b5 from copolymers of acrylic acid esters with methacrylic acid.

Preferred acrylic acid esters are methyl acrylate and ethyl acrylate, wherein the latter is particularly preferred.

Particularly preferred inventive agents comprise copolymers of acrylic acid esters with methacrylic acids as the copolymer b5, said copolymers having a molar mass of 100 to 500 kDa, preferably from 150 to 400 kDa, more preferably from 200 to 300 kDa and particularly from 225 to 275 kDa.

Copolymers b5 are preferably employed within specific quantitative ranges. Here, preferred inventive agents comprise, based on total weight of the ready-for-use agent, 0.05 to 5 wt. %, preferably 0.1 to 4 wt. % and particularly 0.25 to 3 wt. % of copolymer(s) b5.

A quite particularly preferred copolymer b5 results from polymerization of methacrylic acid with ethyl acrylate and is named according to the INCI nomenclature as Acrylates Copolymer. A polymer of this type is available, for example, under the trade name Luviflex® Soft (BASF).

The present invention is not restricted in regard to the choice of the polymers A and B. Only one polymer as well as a plurality of polymers can be employed from the individual described classes. Particularly preferred agents comprise—
(1) copolymer A1+polymer b1
(2) copolymer A1+copolymer b2
(3) copolymer A1+copolymer b3
(4) copolymer A1+copolymer b4-2
(5) copolymer A1+copolymer b5
(6) copolymer A1+polymer b1+copolymer b2
(7) copolymer A1+polymer b1+copolymer b3
(8) copolymer A1+polymer b1+copolymer b4-2
(9) copolymer A1+polymer b1+copolymer b5
(10) copolymer A1+copolymer b2+copolymer b3
(11) copolymer A1+copolymer b2+copolymer b4-2
(12) copolymer A1+copolymer b2+copolymer b5
(13) copolymer A1+copolymer b3+copolymer b4-2
(14) copolymer A1+copolymer b3+copolymer b5
(15) copolymer A1+copolymer b4-2+copolymer b5
(16) copolymer A1+polymer b1+copolymer b2+copolymer b3
(17) copolymer A1+polymer b1+copolymer b2+copolymer b4-2
(18) copolymer A1+polymer b1+copolymer b2+copolymer b5
(19) copolymer A1+polymer b1+copolymer b3+copolymer b4-2
(20) copolymer A 1+polymer b1+copolymer b3+copolymer b5
(21) copolymer A1+polymer b1+copolymer b4-2+copolymer b5
(22) copolymer A1+copolymer b2+copolymer b3+copolymer b4-2
(23) copolymer A1+copolymer b2+copolymer b3+copolymer b5
(24) copolymer A1+copolymer b2+copolymer b4-2+copolymer b5
(25) copolymer A1+copolymer b3+copolymer b4-2+copolymer b5
(26) copolymer A1+polymer b1+copolymer b2+copolymer b3+copolymer b4-2

(27) copolymer A1+polymer b1+copolymer b2+copolymer b3+copolymer b5
(28) copolymer A1+polymer b1+copolymer b2+copolymer b4-2+copolymer b5
(29) copolymer A1+polymer b1+copolymer b3+copolymer b4-2+copolymer b5
(30) copolymer A1+copolymer b2+copolymer b3+copolymer b4-2+copolymer b5
(31) copolymer A1+polymer b1+copolymer b2+copolymer b3+copolymer b4-2+copolymer b5
(32) copolymer A2+polymer b1
(33) copolymer A2+copolymer b2
(34) copolymer A2+copolymer b3
(35) copolymer A2+copolymer b4-2
(36) copolymer A2+copolymer b5
(37) copolymer A2+polymer b1+copolymer b2
(38) copolymer A2+polymer b1+copolymer b3
(39) copolymer A2+polymer b1+copolymer b4-2
(40) copolymer A2+polymer b1+copolymer b5
(41) copolymer A2+copolymer b2+copolymer b3
(42) copolymer A2+copolymer b2+copolymer b4-2
(43) copolymer A2+copolymer b2+copolymer b5
(44) copolymer A2+copolymer b3+copolymer b4-2
(45) copolymer A2+copolymer b3+copolymer b5
(46) copolymer A2+copolymer b4-2+copolymer b5
(47) copolymer A2+polymer b1+copolymer b2+copolymer b3
(48) copolymer A2+polymer b1+copolymer b2+copolymer b4-2
(49) copolymer A2+polymer b1+copolymer b2+copolymer b5
(50) copolymer A2+polymer b1+copolymer b3+copolymer b4-2
(51) copolymer A2+polymer b1+copolymer b3+copolymer b5
(52) copolymer A2+polymer b1+copolymer b4-2+copolymer b5
(53) copolymer A2+copolymer b2+copolymer b3+copolymer b4-2
(54) copolymer A2+copolymer b2+copolymer b3+copolymer b5
(55) copolymer A2+copolymer b2+copolymer b4-2+copolymer b5
(56) copolymer A2+copolymer b3+copolymer b4-2+copolymer b5
(57) copolymer A2+polymer b1+copolymer b2+copolymer b3+copolymer b4-2
(58) copolymer A2+polymer b1+copolymer b2+copolymer b3+copolymer b5
(59) copolymer A2+polymer b1+copolymer b2+copolymer b4-2+copolymer b5
(60) copolymer A2+polymer b1+copolymer b3+copolymer b4-2+copolymer b5
(61) copolymer A2+copolymer b2+copolymer b3+copolymer b4-2+copolymer b5
(62) copolymer A2+polymer b1+copolymer b2+copolymer b3+copolymer b4-2+copolymer b5
(63) copolymer A3+polymer b1
(64) copolymer A3+copolymer b2
(65) copolymer A3+copolymer b3
(66) copolymer A3+copolymer b4-2
(67) copolymer A3+copolymer b5
(68) copolymer A3+polymer b1+copolymer b2
(69) copolymer A3+polymer b1+copolymer b3
(70) copolymer A3+polymer b1+copolymer b4-2
(71) copolymer A3+polymer b1+copolymer b5
(72) copolymer A3+copolymer b2+copolymer b3
(73) copolymer A3+copolymer b2+copolymer b4-2
(74) copolymer A3+copolymer b2+copolymer b5
(75) copolymer A3+copolymer b3+copolymer b4-2
(76) copolymer A3+copolymer b3+copolymer b5
(77) copolymer A3+copolymer b4-2+copolymer b5
(78) copolymer A3+polymer b1+copolymer b2+copolymer b3
(79) copolymer A3+polymer b1+copolymer b2+copolymer b4-2
(80) copolymer A3+polymer b1+copolymer b2+copolymer b5
(81) copolymer A3+polymer b1+copolymer b3+copolymer b4-2
(82) copolymer A3+polymer b1+copolymer b3+copolymer b5
(83) copolymer A3+polymer b1+copolymer b4-2+copolymer b5
(84) copolymer A3+copolymer b2+copolymer b3+copolymer b4-2
(85) copolymer A3+copolymer b2+copolymer b3+copolymer b5
(86) copolymer A3+copolymer b2+copolymer b4-2+copolymer b5
(87) copolymer A3+copolymer b3+copolymer b4-2+copolymer b5
(88) copolymer A3+polymer b1+copolymer b2+copolymer b3+copolymer b4-2
(89) copolymer A3+polymer b1+copolymer b2+copolymer b3+copolymer b5
(90) copolymer A3+polymer b1+copolymer b2+copolymer b4-2+copolymer b5
(91) copolymer A3+polymer b1+copolymer b3+copolymer b4-2+copolymer b5
(92) copolymer A3+copolymer b2+copolymer b3+copolymer b4-2+copolymer b5
(93) copolymer A3+polymer b1+copolymer b2+copolymer b3+copolymer b4-2+copolymer b5
(94) copolymer A1+polymer A2+copolymer b1
(95) copolymer A1+copolymer A2+copolymer b2
(96) copolymer A1+copolymer A2+copolymer b3
(97) copolymer A1+copolymer A2+copolymer b4-2
(98) copolymer A1+copolymer A2+copolymer b5
(99) copolymer A1+polymer A2+copolymer b1+copolymer b2
(100) copolymer A1+polymer A2+copolymer b1+copolymer b3
(101) copolymer A1+polymer A2+copolymer b1+copolymer b4-2
(102) copolymer A1+polymer A2+copolymer b1+copolymer b5
(103) copolymer A1+copolymer A2+copolymer b2+copolymer b3
(104) copolymer A1+copolymer A2+copolymer b2+copolymer b4-2
(105) copolymer A1+copolymer A2+copolymer b2+copolymer b5
(106) copolymer A1+copolymer A2+copolymer b3+copolymer b4-2
(107) copolymer A1+copolymer A2+copolymer b3+copolymer b5
(108) copolymer A1+copolymer A2+copolymer b4-2+copolymer b5
(109) copolymer A1+polymer A2+copolymer b1+copolymer b2+copolymer b3
(110) copolymer A1+polymer A2+copolymer b1+copolymer b2+copolymer b4-2

(111) copolymer A1+polymer A2+copolymer b1+copolymer b2+copolymer b5
(112) copolymer A1+polymer A2+copolymer b1+copolymer b3+copolymer b4-2
(113) copolymer A1+polymer A2+copolymer b1+copolymer b3+copolymer b5
(114) copolymer A1+polymer A2+copolymer b1+copolymer b4-2+copolymer b5
(115) copolymer A1+copolymer A2+copolymer b2+copolymer b3+copolymer b4-2
(116) copolymer A1+copolymer A2+copolymer b2+copolymer b3+copolymer b5
(117) copolymer A1+copolymer A2+copolymer b2+copolymer b4-2+copolymer b5
(118) copolymer A1+copolymer A2+copolymer b3+copolymer b4-2+copolymer b5
(119) copolymer A1+polymer A2+copolymer b1+copolymer b2+copolymer b3+copolymer b4-2
(120) copolymer A1+polymer A2+copolymer b1+copolymer b2+copolymer b3+copolymer b5
(121) copolymer A1+polymer A2+copolymer b1+copolymer b2+copolymer b4-2+copolymer b5
(122) copolymer A1+polymer A2+copolymer b1+copolymer b3+copolymer b4-2+copolymer b5
(123) copolymer A1+copolymer A2+copolymer b2+copolymer b3+copolymer b4-2+copolymer b5
(124) copolymer A1+polymer A2+copolymer b1+copolymer b2+copolymer b3+copolymer b4-2+copolymer b5
(125) copolymer A1+polymer A3+copolymer b1
(126) copolymer A1+copolymer A3+copolymer b2
(127) copolymer A1+copolymer A3+copolymer b3
(128) copolymer A1+copolymer A3+copolymer b4-2
(129) copolymer A1+copolymer A3+copolymer b5
(130) copolymer A1+polymer A3+copolymer b1+copolymer b2
(131) copolymer A1+polymer A3+copolymer b1+copolymer b3
(132) copolymer A1+polymer A3+copolymer b1+copolymer b4-2
(133) copolymer A1+polymer A3+copolymer b1+copolymer b5
(134) copolymer A1+copolymer A3+copolymer b2+copolymer b3
(135) copolymer A1+copolymer A3+copolymer b2+copolymer b4-2
(136) copolymer A1+copolymer A3+copolymer b2+copolymer b5
(137) copolymer A1+copolymer A3+copolymer b3+copolymer b4-2
(138) copolymer A1+copolymer A3+copolymer b3+copolymer b5
(139) copolymer A1+copolymer A3+copolymer b4-2+copolymer b5
(140) copolymer A1+polymer A3+copolymer b1+copolymer b2+copolymer b3
(141) copolymer A1+polymer A3+copolymer b1+copolymer b2+copolymer b4-2
(142) copolymer A1+polymer A3+copolymer b1+copolymer b2+copolymer b5
(143) copolymer A1+polymer A3+copolymer b1+copolymer b3+copolymer b4-2
(144) copolymer A1+polymer A3+copolymer b1+copolymer b3+copolymer b5
(145) copolymer A1+polymer A3+copolymer b1+copolymer b4-2+copolymer b5
(146) copolymer A1+copolymer A3+copolymer b2+copolymer b3+copolymer b4-2
(147) copolymer A1+copolymer A3+copolymer b2+copolymer b3+copolymer b5
(148) copolymer A1+copolymer A3+copolymer b2+copolymer b4-2+copolymer b5
(149) copolymer A1+copolymer A3+copolymer b3+copolymer b4-2+copolymer b5
(150) copolymer A1+polymer A3+copolymer b1+copolymer b2+copolymer b3+copolymer b4-2
(151) copolymer A1+polymer A3+copolymer b1+copolymer b2+copolymer b3+copolymer b5
(152) copolymer A1+polymer A3+copolymer b1+copolymer b2+copolymer b4-2+copolymer b5
(153) copolymer A1+polymer A3+copolymer b1+copolymer b3+copolymer b4-2+copolymer b5
(154) copolymer A1+copolymer A3+copolymer b2+copolymer b3+copolymer b4-2+copolymer b5
(155) copolymer A1+polymer A3+copolymer b1+copolymer b2+copolymer b3+copolymer b4-2+copolymer b5
(156) copolymer A2+polymer A3+copolymer b1
(157) copolymer A2+copolymer A3+copolymer b2
(158) copolymer A2+copolymer A3+copolymer b3
(159) copolymer A2+copolymer A3+copolymer b4-2
(160) copolymer A2+copolymer A3+copolymer b5
(161) copolymer A2+copolymer A3+polymer b1+copolymer b2
(162) copolymer A2+copolymer A3+polymer b1+copolymer b3
(163) copolymer A2+copolymer A3+polymer b1+copolymer b4-2
(164) copolymer A2+copolymer A3+polymer b1+copolymer b5
(165) copolymer A2+copolymer A3+copolymer b2+copolymer b3
(166) copolymer A2+copolymer A3+copolymer b2+copolymer b4-2
(167) copolymer A2+copolymer A3+copolymer b2+copolymer b5
(168) copolymer A2+copolymer A3+copolymer b3+copolymer b4-2
(169) copolymer A2+copolymer A3+copolymer b3+copolymer b5
(170) copolymer A2+copolymer A3+copolymer b4-2+copolymer b5
(171) copolymer A2+polymer A3+copolymer b1+copolymer b2+copolymer b3
(172) copolymer A2+copolymer A3+polymer b1+copolymer b2+copolymer b4-2
(173) copolymer A2+copolymer A3+polymer b1+copolymer b2+copolymer b5
(174) copolymer A2+copolymer A3+polymer b1+copolymer b3+copolymer b4-2
(175) copolymer A2+copolymer A3+polymer b1+copolymer b3+copolymer b5
(176) copolymer A2+copolymer A3+polymer b1+copolymer b4-2+copolymer b5
(177) copolymer A2+copolymer A3+copolymer b2+copolymer b3+copolymer b4-2
(178) copolymer A2+copolymer A3+copolymer b2+copolymer b3+copolymer b5
(179) copolymer A2+copolymer A3+copolymer b2+copolymer b4-2+copolymer b5
(180) copolymer A2+copolymer A3+copolymer b3+copolymer b4-2+copolymer b5
(181) copolymer A2+copolymer A3+polymer b1+copolymer b2+copolymer b3+copolymer b4-2
(182) copolymer A2+copolymer A3+polymer b1+copolymer b2+copolymer b3+copolymer b5

(183) copolymer A2+copolymer A3+polymer b1+copolymer b2+copolymer b4-2+copolymer b5
(184) copolymer A2+copolymer A3+polymer b1+copolymer b3+copolymer b4-2+copolymer b5
(185) copolymer A2+copolymer A3+copolymer b2+copolymer b3+copolymer b4-2+copolymer b5
(186) copolymer A2+copolymer A3+polymer b1+copolymer b2+copolymer b3+copolymer b4-2+copolymer b5
(187) copolymer A1+copolymer A2+copolymer A3+copolymer b1
(188) copolymer A1+copolymer A2+copolymer A3+copolymer b2
(189) copolymer A1+copolymer A2+copolymer A3+copolymer b3
(190) copolymer A1+copolymer A2+copolymer A3+copolymer b4-2
(191) copolymer A1+copolymer A2+copolymer A3+copolymer b5
(192) copolymer A1+copolymer A2+copolymer A3+polymer b1+copolymer b2
(193) copolymer A1+copolymer A2+copolymer A3+polymer b1+copolymer b3
(194) copolymer A1+copolymer A2+copolymer A3+polymer b1+copolymer b4-2
(195) copolymer A1+copolymer A2+copolymer A3+polymer b1+copolymer b5
(196) copolymer A1+copolymer A2+copolymer A3+copolymer b2+copolymer b3
(197) copolymer A1+copolymer A2+copolymer A3+copolymer b2+copolymer b4-2
(198) copolymer A1+copolymer A2+copolymer A3+copolymer b2+copolymer b5
(199) copolymer A1+copolymer A2+copolymer A3+copolymer b3+copolymer b4-2
(200) copolymer A1+copolymer A2+copolymer A3+copolymer b3+copolymer b5
(201) copolymer A1+copolymer A2+copolymer A3+copolymer b4-2+copolymer b5
(202) copolymer A1+copolymer A2+copolymer A3+polymer b1+copolymer b2+copolymer b3
(203) copolymer A1+copolymer A2+copolymer A3+polymer b1+copolymer b2+copolymer b4-2
(204) copolymer A1+copolymer A2+copolymer A3+polymer b1+copolymer b2+copolymer b5
(205) copolymer A1+copolymer A2+copolymer A3+polymer b1+copolymer b3+copolymer b4-2
(206) copolymer A1+copolymer A2+copolymer A3+polymer b1+copolymer b3+copolymer b5
(207) copolymer A1+copolymer A2+copolymer A3+polymer b1+copolymer b4-2+copolymer b5
(208) copolymer A1+copolymer A2+copolymer A3+copolymer b2+copolymer b3+copolymer b4-2
(209) copolymer A1+copolymer A2+copolymer A3+copolymer b2+copolymer b3+copolymer b5
(210) copolymer A1+copolymer A2+copolymer A3+copolymer b2+copolymer b4-2+copolymer b5
(211) copolymer A1+copolymer A2+copolymer A3+copolymer b3+copolymer b4-2+copolymer b5
(212) copolymer A1+copolymer A2+copolymer A3+polymer b1+copolymer b2+copolymer b3+copolymer b4-2
(213) copolymer A1+copolymer A2+copolymer A3+polymer b1+copolymer b2+copolymer b3+copolymer b5
(214) copolymer A1+copolymer A2+copolymer A3+polymer b1+copolymer b2+copolymer b4-2+copolymer b5
(215) copolymer A1+copolymer A2+copolymer A3+polymer b1+copolymer b3+copolymer b4-2+copolymer b5
(216) copolymer A1+copolymer A2+copolymer A3+copolymer b2+copolymer b3+copolymer b4-2+copolymer b5
(217) copolymer A1+copolymer A2+copolymer A3+polymer b1+copolymer b2+copolymer b3+copolymer b4-2+copolymer b5

Regardless of which of the 217 preferred polymer combinations is selected, agents according to the invention are preferred in which the weight ratio of polymer(s) A to polymer(s) B is 10:1 to 1:10, preferably 8:1 to 1:8, more preferably 5:1 to 1:5 and especially 4:1 to 1:4.

Regardless of the type and weight ratio of the polymers to one another, inventive agents are moreover preferred in which total polymer content of the agent is 1 to 15 wt. %, preferably 2.5 to 12.5 wt. %, more preferably 4 to 10 wt. % and especially 5 to 8 wt. %.

Agents according to the invention comprise the polymers in a cosmetically acceptable carrier.

Preferred cosmetically acceptable carriers are aqueous, alcoholic or aqueous alcoholic media containing preferably at least 10 wt. % water, based on total agent. In particular, lower alcohols containing 1 to 4 carbon atoms such as ethanol and isopropanol, commonly used for cosmetic purposes, can be comprised as alcohols.

Organic solvents or a mixture thereof with a boiling point of less than 400° C. can be comprised as the additional co-solvents in a quantity of 0.1 to 15 wt. %, preferably 1 to 10 wt. %, based on total agent. Particularly suitable additional co-solvents include unbranched or branched hydrocarbons such as pentane, hexane and isopentane, and cyclic hydrocarbons such as cyclopentane and cyclohexane. Additional, particularly preferred water-soluble solvents include glycerine, ethylene glycol, butylene glycol and propylene glycol in an amount of up to 30 wt. % based on total agent.

The agents preferably exhibit a pH of 2 to 11. The pH range is particularly preferably between 4 and 9. In the context of this publication, pH data refer to the pH at 25° C. unless otherwise stated.

Agents according to the invention can additionally comprise auxiliaries and additives typically incorporated into each cosmetic.

Care substances may be mentioned as suitable auxiliaries and additives. They find use both in skin treatment agents and hair treatment agents and, depending on the choice of the care substance, can be incorporated, for example, into creams, shampoos, hair rinses, gels, pump and aerosol sprays and foam products.

Silicone oil and/or silicone gum for example, can be employed as the care substance. In a particular embodiment of the invention, the agents comprise at least one silicone oil and/or silicone gum.

Suitable silicone oils or silicone gums according to the invention include dialkyl and alkylarylsiloxanes, such as, dimethylpolysiloxane and methylphenylpolysiloxane, as well as their alkoxylated, quaternized or also anionic derivatives. Cyclic and linear polydialkylsiloxanes, their alkoxylated and/or aminated derivatives, dihydroxypolydimethylsiloxanes and polyphenylalkylsiloxanes are preferred.

Silicone oils afford the most varied effects. Thus, for example, they simultaneously influence dry and wet combability, feel of dry and wet hair, and hair gloss. The term "silicone oils" is understood by the person skilled in the art to mean organosilicon compounds with a plurality of structures. Among these are Dimethiconols (S1). These can be linear, branched, cyclic, or cyclic and branched. Linear Dimethi conols can be represented by the following structural formula (S1-I)—

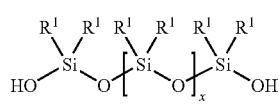
(S1-I)

Branched Dimethiconols can be represented by the following structural formula (S1-II):

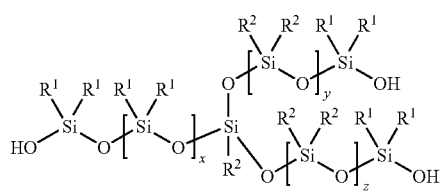
(S1-II)

$R^1$ and $R^2$ are each independently hydrogen, a methyl group, a $C_2$ to $C_{30}$ linear, saturated or unsaturated hydrocarbon group, a phenyl group and/or an aryl group. Non-limiting examples of $R^1$ and $R^2$ include alkyl groups such as methyl, ethyl, propyl, isopropyl, isopropyl, butyl, isobutyl, pentyl, isopentyl, neopentyl, amyl, isoamyl, hexyl, isohexyl and the like; alkenyl groups such as vinyl, halogenovinyl, alkylvinyl, allyl, halogenoallyl, alkylallyl; cycloalkyl groups such as cyclobutyl, cyclopentyl, cyclohexyl and the like; phenyl groups, benzyl groups, halogenated hydrocarbon groups such as 3-chloropropyl, 4-bromobutyl, 3,3,3-trifluoropropyl, chlorocyclohexyl, bromophenyl, chlorophenyl and the like as well; as sulfur-containing groups, such as mercaptoethyl, mercaptopropyl, mercaptohexyl, mercaptophenyl and the like. Advantageously $R^1$ and $R^2$ are an alkyl group comprising 1 to about 6 carbon atoms; preferably $R^1$ and $R^2$ are methyl. The numbers x, y and z are whole numbers, and each independently range from 0 to 50,000. Molar weights of the Dimethiconols lie from about 1000 D to about 10,000,000 D. The viscosities range from about 100 to about 10,000,000 cPs, measured at 25° C. with a glass capillary viscosimeter following the Dow Corning Corporate Test Method CTM 0004 of 20 Jul. 1970. Preferred viscosities are from about 1000 to about 5,000,000 cPs; particularly preferred viscosities are from about 10,000 to about 3,000,000 cPs. The most preferred range is from about 50,000 to about 2,000,000 cPs.

Dimethicones (S2) form the second group of the silicones that can be comprised according to the invention. They can be linear, branched, cyclic, or cyclic and branched. Linear Dimethicones can be represented by the following structural formula (S2-I)—

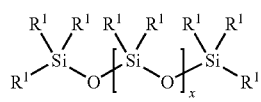
(S2-I)

Branched Dimethicones can be represented by the structural formula (S2-II)—

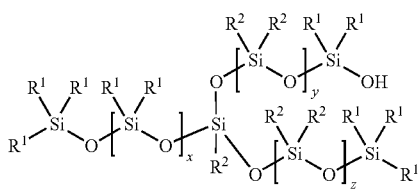
(S2-II)

$R^1$ and $R^2$ are each independently hydrogen, a methyl group, a $C_2$ to $C_{30}$ linear, saturated or unsaturated hydrocarbon group, a phenyl group and/or an aryl group. Non-limiting examples of $R^1$ and $R^2$ include alkyl groups such as methyl, ethyl, propyl, isopropyl, isopropyl, butyl, isobutyl, pentyl, isopentyl, neopentyl, amyl, isoamyl, hexyl, isohexyl and the like; alkenyl groups, such as vinyl, halogenovinyl, alkylvinyl, allyl, halogenoallyl, alkylallyl; cycloalkyl groups such as cyclobutyl, cyclopentyl, cyclohexyl and the like; phenyl groups, benzyl groups, halogenated hydrocarbon groups such as 3-chloropropyl, 4-bromobutyl, 3,3,3-trifluoropropyl, chlorocyclohexyl, bromophenyl, chlorophenyl and the like; as well as sulfur-containing groups such as mercaptoethyl, mercaptopropyl, mercaptohexyl, mercaptophenyl and the like. Advantageously $R^1$ and $R^2$ are an alkyl group comprising 1 to about 6 carbon atoms; preferably $R^1$ and $R^2$ are methyl. The numbers x, y and z are whole numbers and each independently range from 0 to 50,000. The molar weights of the Dimethicones lie from about 1000 D to about 10,000,000 D. The viscosities range from about 100 to about 10,000,000 cPs, measured at 25° C. with a glass capillary viscosimeter following the Dow Corning Corporate Test Method CTM 0004 of 20 Jul. 1970. Preferred viscosities are from about 1000 to about 5,000,000 cPs; particularly preferred viscosities are from about 10,000 to about 3,000,000 cPs. The most preferred range is from about 50,000 to about 2,000,000 cPs.

Dimethicone copolyols (S3) form a further group of suitable silicones. Dimethicone copolyols can be represented by the following structural formulae—

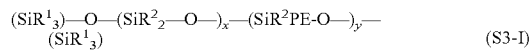
(S3-I)

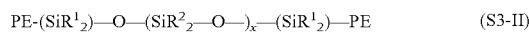
(S3-II)

Branched Dimethicone copolyols can be represented by the following structural formula (S3-III)—

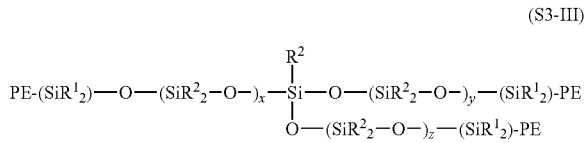
(S3-III)

or by the structural formula (S3-IV)—

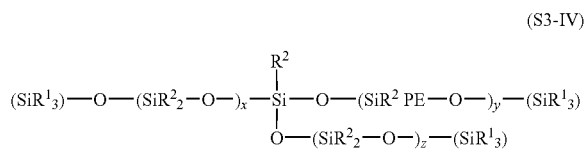
(S3-IV)

$R^1$ and $R^2$ are each independently hydrogen, a methyl group, a $C_2$ to $C_{30}$ linear, saturated or unsaturated hydrocarbon group, a phenyl group and/or an aryl group. Non-limiting examples of $R^1$ and $R^2$ include alkyl groups such as methyl, ethyl, propyl, isopropyl, isopropyl, butyl, isobutyl, pentyl, isopentyl, neopentyl, amyl, isoamyl, hexyl, isohexyl and the like; alkenyl groups such as vinyl, halogenovinyl, alkylvinyl, allyl, halogenoallyl, alkylallyl; cycloalkyl groups such as cyclobutyl, cyclopentyl, cyclohexyl and the like; phenyl groups, benzyl groups, halogenated hydrocarbon groups such as 3-chloropropyl, 4-bromobutyl, 3,3,3-trifluoropropyl, chlorocyclohexyl, bromophenyl, chlorophenyl and the like; as well as sulfur-containing groups such as mercaptoethyl, mercaptopropyl, mercaptohexyl, mercaptophenyl and the like. Advantageously $R^1$ and $R^2$ are an alkyl group comprising 1 to about 6 carbon atoms; preferably $R^1$ and $R^2$ are methyl. PE is a polyoxyalkylene group. Preferred polyoxyalkylene groups are derived from ethylene oxide, propylene oxide and glycerine. The numbers x, y and z are whole numbers and each independently range from 0 to 50,000. The molar weights of the Dimethicones lie from about 1000 D to about 10,000,000 D. The viscosities range from about 100 and 10 000 000 cPs, measured at 25° C. with a glass capillary viscosimeter following the Dow Corning Corporate Test Method CTM 0004 of 20 Jul. 1970. Preferred viscosities are from about 1000 to about 5,000,000 cPs; quite particularly preferred viscosities are from about 10,000 to about 3,000,000 cPs. The most preferred range is from about 50,000 to about 2,000,000 cPs.

Suitable Dimethicone copolyols are commercially available and are marketed for example by Dow Corning under the trade name Dow Corning® 5330 Fluid.

Naturally, the teaching according to the invention also includes the fact that the Dimethiconols, Dimethicones and/or Dimethicone copolymers can already be present as an emulsion. The corresponding emulsions of the Dimethiconols, Dimethicones and/or Dimethicone copolymers can be produced both after the production of the corresponding Dimethiconols, Dimethicones and/or Dimethicone copolymers from these and the usual emulsification processes known to the person skilled in the art. Cationic, anionic, non-ionic or zwitterionic surfactants and emulsifiers can be used as auxiliaries and adjuvants for the production of the corresponding emulsions. Naturally, the emulsions of the Dimethiconols, Dimethicones and/or Dimethicone copolymers can also be produced directly by an emulsion polymerization process. These types of processes are also well known to the person skilled in the art.

When the Dimethiconols, Dimethicones and/or Dimethicone copolymers are used as an emulsion, then according to the invention, the droplet size of the emulsified particles ranges from about 0.01 to about 10,000 μm, preferably about 0.01 to about 100 μm, particularly preferably about 0.01 to about 20 μm and quite particularly preferably about 0.01 to about 10 μm. Particle size is determined according to the light scattering method.

If branched Dimethiconols, Dimethicones and/or Dimethicone copolymers are used, then it can be taken as understood that the branching is greater than a fortuitous branching that accidentally results from impurities in the respective monomers. Accordingly, in the context of the present invention, the degree of branching is understood to be greater than 0.01% for branched Dimethiconols, Dimethicones and/or Dimethicone copolymers. The degree of branching is preferably greater than 0.1% and quite particularly preferably greater than 0.5%. The degree of branching is determined from the ratio of the unbranched monomers to the branched monomers (i.e., the amount of tri and tetrafunctional siloxanes). According to the invention, both low-branched as well as highly branched Dimethiconols, Dimethicones and/or Dimethicone copolymers can be quite particularly preferred.

Further suitable silicones are amino functional silicones (S4), especially the silicones compiled under the INCI name Amodimethicone. These are understood to be silicones that possess at least one, optionally substituted, amino group.

Such silicones can be described, for example, by the Formula (S4-I)—

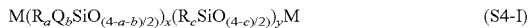

$$M(R_aQ_bSiO_{(4-a-b)/2})_x(R_cSiO_{(4-c)/2})_yM \quad \text{(S4-I)}$$

wherein R is a hydrocarbon or a hydrocarbon group with 1 to 6 carbon atoms; Q is a polar group of the general formula —$R^1Z$, wherein $R^1$ is a divalent, linking group that is bonded to hydrogen and Z is made up of carbon atoms and hydrogen atoms, carbon-, hydrogen- and oxygen atoms or carbon-, hydrogen- and nitrogen atoms, and Z is an organic amino functionalized group having at least one amino functional group; "a" is a value in the range of about 0 to about 2, "b" is a value in the range of about 1 to about 3, "a"+"b" is less than or equal to 3, and "c" is a number in the range of about 1 to about 3; x is a number in the range of 1 to about 2000, advantageously from about 3 to about 50, and most preferably from about 3 to about 25; y is a number in the range of about 20 to about 10,000, advantageously from about 125 to about 10,000, and most preferably from about 150 to about 1000; and M is a suitable silicone end-group as known from the prior art, preferably trimethylsiloxy.

Z is an organic, amino functional group comprising at least one functional amino group. A possible formula for Z is $NH(CH_2)_zNH_2$, wherein z stands for a whole number from 1 to 50. Another possible formula for Z is —$NH(CH_2)_zNH(CH_2)_{zz}$, in which both z and also zz independently of one another stand for a whole number from 1 to 50, wherein this structure includes diamino ring structures, such as piperazinyl. Particularly preferably, Z is a —$NHCH_2CH_2NH_2$ group. Another possible formula for Z is —$N(CH_2)_zNX^1X^2$ or —$NX^1X^2$, in which $X^1$ and $X^2$ is each independently selected from hydrogen and a hydrocarbon group containing 1 to about 6 carbon atoms.

Q stands quite particularly preferably for a polar, amino functional group of the Formula —$CH_2CH_2CH_2NHCH_2CH_2NH_2$.

The molar ratio of the $R_aQ_b SiO_{(4-a-b)/2}$ units to the $R_cSiO_{(4-c)/2}$ units is in the range from about 1:2 to 1:65, preferably from about 1:5 to about 1:65 and particularly preferably from about 1:15 to about 1:20. If one or a plurality of silicones of the above Formula are added, then the different variable substituents in the above Formula for the different silicone components that are present in the silicone mixture can be different.

Preferred amino functional silicones correspond to the Formula (S4-II)—

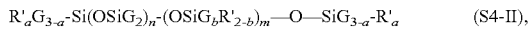

$$R'_aG_{3-a}\text{-}Si(OSiG_2)_n\text{-}(OSiG_bR'_{2-b})_m\text{—O—}SiG_{3-a}\text{-}R'_a \quad \text{(S4-II),}$$

wherein:

G is —H, a phenyl group, —OH, —O—$CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$;

a is a number from 0 to 3, particularly 0;

b is a number from 0 to 1, particularly 1, m and n are numbers whose sum (m+n) is from 1 to 2000, preferably from 50 to 150, wherein n preferably assumes values of 0 to 1999 and particularly 49 to 149 and m preferably assumes values of 1 to 2000, particularly 1 to 10, and R' is a monovalent group chosen from
—N(R")—CH$_2$—CH$_2$—N(R")$_2$
—N(R")$_2$
—N$^+$(R")$_3$A$^-$
—N$^+$H(R")$_2$A$^-$
—N$^+$H$_2$(R")A$^-$ and
—N(R")—CH$_2$—CH$_2$—N$^+$R"H$_2$A$^-$, wherein each R" is the same or different group from —H, -phenyl, -benzyl, and C$_{1-20}$ alkyl groups, preferably —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, and —C(CH$_3$)$_3$; and K is an anion preferably chosen from chloride, bromide, iodide or methosulfate.

Particularly preferred amino functional silicones correspond to the Formula (S4-III)—

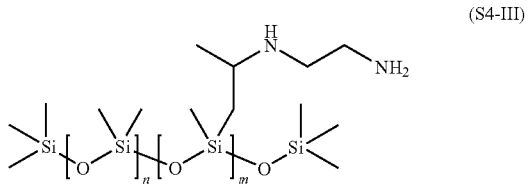

wherein m and n are numbers whose sum (m+n) is from 1 to 2000, preferably from 50 to 150, wherein n preferably assumes values of 0 to 1999 and particularly from 49 to 149 and m preferably assumes values of 1 to 2000, particularly 1 to 10. These silicones are designated according to the INCI nomenclature as Trimethylsilylamodimethicones Further amino functional silicones of the Formula (S4-IV) are particularly preferred—

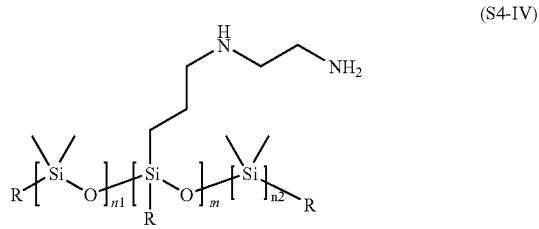

wherein R is —OH, —O—CH$_3$ or a —CH$_3$ group: and m, n1 and n2 are numbers whose sum (m+n1+n2) is between 1 and 2000, preferably between 50 and 150, wherein the sum (n1+n2) preferably assumes values of 0 to 1999, particularly from 49 to 149, and m preferably assumes values of 1 to 2000, particularly 1 to 10.

These silicones are designated as Amodimethicones according to INCI nomenclature and are available, for example, in the form of an emulsion as the commercial product Dow Corning® 949 in a mixture with a cationic and a non-ionic surfactant.

Preferably, amino functional silicones are employed having an amine number of 0.25 meq/g or greater, preferably 0.3 meq/g or greater, and particularly preferably 0.4 meq/g or greater. The amine number refers to milli-equivalents of amine per gram of amino functional silicone. It can be measured by titration and is also reported with the unit mg KOH/g.

Further suitable silicones include—
oligomeric polydimethylcyclosiloxanes (INCI name: Cyclomethicones), especially the tetrameric and the pentameric compound commercially available as the products DC 245 Fluid, DC 344 or DC 345 by Dow Corning;
hexamethyldisiloxane (INCI name: Hexamethyldisiloxane) (e.g., the product marketed under the trade name Abil® K 520);
polyphenylmethylsiloxane (INCI name: Phenyl Trimethicone) (e.g., the commercial product DC 556 Cosmetic Grade Fluid from Dow Corning);
esters and partial esters of silicone-glycol copolymers (e.g., commercialized by Fanning Company under the trade name Fancorsil® LIM) (INCI name: Dimethicone Copolyol Meadowfoamate); and
anionic silicone oils such as the product Dow Corning® 1784.

According to a preferred embodiment, the agent according to the invention comprises at least two different silicone derivatives, in particular a combination of a volatile and a non-volatile silicone. In the context of the invention, volatile silicones are those that exhibit a volatility that is the same or greater than the volatility of the cyclic, pentameric dimethylsiloxane. Such combinations are also available as commercial products (e.g., Dow Corning® 1401, Dow Corning® 1403 and Dow Corning® 1501, each being mixtures of a Cyclomethicone and a Dimethiconol).

Preferred mixtures of different silicones include Dimethicones and Dimethiconols, linear Dimethicones and cyclic Dimethiconols. A particularly preferred mixture of silicones includes at least one cyclic Dimethiconol and/or Dimethicone, at least one additional non-cyclic Dimethicone and/or Dimethiconol as well as at least one amino functional silicone.

If different silicones are used as a mixture, then the mixing ratio can be varied over a wide range. Preferably, however, all of the silicones used in the mixture are employed in a ratio of 5:1 to 1:5 in the case of a binary mixture. A ratio of 3:1 to 1:3 is particularly preferred. Quite particularly preferred mixtures comprise as far as possible all silicones comprised in the mixture in a ratio of about 1:1, each based on added quantities in wt. %.

The agents preferably comprise silicones in amounts of 1 to 25 wt. %, particularly preferably in amounts of 5 to 20 wt. % and particularly preferably in amounts of 7 to 15 wt. %, based on total agent.

Although the agent according to the invention preferably comprises a silicone derivative as a conditioning component, it is also possible that the agent includes at least one conditioner from another compound class instead of or in addition to a silicone component.

The agent can comprise, for example, at least one protein hydrolyzate and/or one of its derivatives as a care substance of another compound class.

Protein hydrolyzates are product mixtures obtained by acid-, base- or enzyme-catalyzed degradation of proteins (albumins). According to the invention, the term "protein hydrolyzates" is also understood to mean total hydrolyzates as well as individual amino acids and their derivatives as well as mixtures of different amino acids. Furthermore, according to the invention, polymers built up from amino acids and amino acid derivatives are understood to be included in the term protein hydrolyzates. The latter include for example polyalanine, polyasparagine, polyserine etc. Additional examples of usable compounds according to the invention are L-alanyl-L-proline, polyglycine, glycyl-L-glutamine or D/L-methionine-S-methyl sulfonium chloride. Of course, β-amino acids and their derivatives, like β-alanine, anthranilic acid or hippuric acid, can also be added according to the invention. The molar weight of the protein hydrolyzates utilizable according to the invention ranges from about 75—the molar weight of glycine—to about 200,000; preferably the molar weight is about 75 to about 50,000, and more preferably about 75 to about 20,000 Dalton.

According to the invention, the added protein hydrolyzates can be vegetal as well as animal, marine or synthetic origin.

Animal protein hydrolyzates include elastin, collagen, keratin, silk protein, and milk protein hydrolyzates, which can also be present in the form of their salts. Such products are marketed, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm) and Kerasol® (Croda).

Protein hydrolyzates of vegetal origin (e.g., soya-, almond-, pea-, potato- and wheat protein hyrolyzates) are available, for example, under the trade names Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

Although it is preferred to add protein hydrolyzates as such, optionally other mixtures containing amino acids can also be added in their place. Likewise, it is possible to add derivatives of protein hydrolyzates (e.g., in the form of their fatty acid condensation products). Such products are marketed, for example, under the trade names Lamepon® (Cognis), Lexein® (Inolex), Crolastin® (Croda), Crosilk® (Croda) or Crotein® (Croda).

Naturally, the invention includes all isomeric forms, such as cis/trans isomers, diastereoisomers and chiral isomers.

According to the invention, it is also possible to use a mixture of a plurality of protein hydrolyzates.

Agents according to the invention comprise protein hydrolyzates, for example, in concentrations of about 0.01 wt. % to about 20 wt. %, preferably about 0.05 wt. % up to about 15 wt. % and quite particularly preferably in amounts of about 0.05 wt. % up to about 5 wt. %, each based on total end-use preparation.

In addition, cationic surfactants are suitable as care substances of another class of compounds.

According to the invention, cationic surfactants of the type quaternary ammonium compounds, the esterquats and the amido amines are preferred. Preferred quaternary ammonium compounds are ammonium halides, particularly chlorides and bromides, such as alkyltrimethylammonium chlorides, dialkyldimethylammonium chlorides and trialkylmethylammonium chlorides (e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride), as well as the imidazolium compounds known under the INCI names Quaternium-27 and Quaternium-83. Long alkyl chains of the above-mentioned surfactants preferably have 10 to 18 carbon atoms.

Esterquats are known compounds having both at least one ester function and also a quaternary ammonium group as structural elements. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are marketed, for example, under the trade names Stepantex®, Dehyquart® and Armocare®. The products Armocare® VGH-70, an N,N-bis(2-Palmitoyloxyethyl)dimethylammonium chloride, as well as Dehyquart® F-75, Dehyquart® C-4046, Dehyquart® L80 and Dehyquart® AU 35 are examples of such esterquats.

Alkylamido amines are normally manufactured by amidation of natural or synthetic fatty acids and fatty acid fractions with dialkylamino amines. According to the invention, a particularly suitable compound from this substance group is represented by stearamidopropyldimethylamine, commercially available under the designation Tegamid® S 18.

Inventive agents preferably comprise cationic surfactants in quantities of 0.05 to 10 wt. %, based on total end-use preparation. Quantities of 0.1 to 5 wt. % are particularly preferred.

Conditioning polymers are also suitable conditioners. It is worth mentioning here that some conditioning polymers also exhibit film-forming and/or setting properties, and consequently can also be named in the listing of suitable film-forming and/or setting polymers.

A first group of conditioning polymers are cationic polymers. Cationic polymers refer to polymers possessing a group in the main chain and/or side chain which can be "temporarily" or "permanently" cationic. "Permanently cationic", according to the invention, refers to those polymers which have a cationic group, independently of the pH of the medium. These are generally polymers having a quaternary nitrogen atom, for example, in the form of an ammonium group. Preferred cationic groups are quaternary ammonium groups. In particular, those polymers in which the quaternary ammonium groups are bonded through a $C_{1-4}$ hydrocarbon group to a polymer backbone of acrylic acid, methacrylic acid or their derivatives, are particularly suitable.

Homopolymers of the general formula (G1-I)—

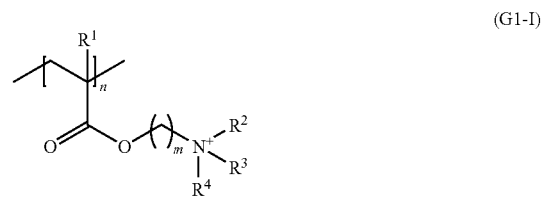

(G1-I)

wherein $R^1$ is —H or —$CH_3$; $R^2$, $R^3$ and $R^4$ are independently chosen from $C_{1-4}$ alkyl, -alkenyl or -hydroxyalkyl groups; m=1, 2, 3 or 4; n is a natural number; and $X^-$ is a physiologically compatible organic or inorganic anion, as well as copolymers consisting of the monomer units listed in formula (GM) and non-ionic monomer units, are particularly preferred cationic polymers. Regarding these polymers, those that are preferred in accordance with the invention meet at least one of the following conditions:

$R^1$ is a methyl group
$R^2$, $R^3$ and $R^4$ are methyl groups
m is 2.

Exemplary physiologically compatible counter ions $X^-$ include halide ions, sulfate ions, phosphate ions, methosulfate ions as well as organic ions such as lactate, citrate, tartrate and acetate ions. Halide ions are preferred, particularly chloride.

A particularly suitable homopolymer is the optionally crosslinked poly(methacryloyloxyethyltrimethylammonium chloride) with the INCI name Polyquaternium-37. Crosslinking can be effected, when desired, with the help of olefinically polyunsaturated compounds (e.g., divinylbenzene, tetraallyloxyethane, methylene bisacrylamide, diallyl ether, polyallyl polyglyceryl ether, or allyl ethers of sugars or sugar derivatives such as erythritol, pentaerythritol, arabitol, mannitol, sorbitol, sucrose or glucose). Methylene bisacrylamide is a preferred crosslinking agent.

The homopolymer is preferably employed in the form of a non-aqueous polymer dispersion having a polymer content of 30 wt. % or greater. Such polymer dispersions are commercially available under the names Salcare® SC 95 (ca. 50% polymer content, additional components: mineral oil (INCI name: Mineral Oil) and tridecyl-polyoxypropylene polyoxyethylene ether (INCI name: PPG-1-Trideceth-6)) and Salcare® SC 96 (ca. 50% polymer content, additional components: mixture of diesters of propylene glycol with a mixture of caprylic- and capric acid (INCI name: Propylene Glycol Dicaprylate/Dicaprate) and tridecyl-polyoxypropylene polyoxyethylene ether (INCI name: PPG-1-Trideceth-6)).

Copolymers with monomer units according to formula (G1-I) preferably comprise acrylamide, methacrylamide, $C_{1-4}$ alkyl esters of acrylic acid and $C_{1-4}$ alkyl esters of methacrylic acid as the non-ionic monomer units. Acrylamide is particularly preferred among these non-ionic monomers. These copolymers can also be crosslinked like the above described homopolymers. An inventively preferred copolymer is the crosslinked acrylamide/methacryloyloxyethyltrimethylammonium chloride copolymer. Such copolymers, wherein the monomers are present in a weight ratio of about 20:80, are commercially available as a ca. 50% conc. non-aqueous polymer dispersion under the trade name Salcare® SC 92.

Further preferred cationic polymers include —
quaternized cellulose derivatives, commercially available under the trade names Celquat® and Polymer JR®. The compounds Celquat® H 100, Celquat® L 200 and Polymer JR®400 are preferred quaternized cellulose derivatives;
cationic alkyl polyglycosides according to DE-PS 44 13 686;
cationized honey, for example, the commercial product Honeyquat® 50;
cationic guar derivatives, such as in particular the products marketed under the trade names Cosmedia® Guar and Jaguar®;
polysiloxanes with quaternary groups, such as, for example, the commercially available products Q2-7224 (manufacturer: Dow Corning; a stabilized trimethylsilylamodimethicone), Dow Corning® 929 emulsion (comprising a hydroxylamino modified silicone, also referred to as amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, Quaternium-80);
polymeric dimethyldiallylammonium salts and their copolymers with esters and amides of acrylic acid and methacrylic acid. The commercially available products Merquat®100 (poly(dimethyldiallylammonium chloride)) and Merquat®550 (dimethyldiallylammonium chloride acrylamide copolymer) are examples of such cationic polymers;
copolymers of vinyl pyrrolidone with quaternized derivatives of dialkylaminoalkyl acrylate and dialkylaminoalkyl methacrylate, such as vinyl pyrrolidone-dimethylaminoethyl methacrylate copolymers quaternized with diethyl sulfate. Such compounds are commercially available under the trade names Gafquat®734 and Gafquat®755;
Vinyl pyrrolidone vinyl imidazolium methochloride copolymers, as are offered under the trade names Luviquat® FC 370, FC 550, FC 905 and HM 552;
quaternized polyvinyl alcohol; and
polymers containing quaternary nitrogen atoms in the main polymer chain and known by the names Polyquaternium 2, Polyquaternium 17, Polyquaternium 18 and Polyquaternium 27.

Polymers designated as Polyquaternium-24 (e.g., the commercial product Quatrisoft® LM 200) can also be employed as cationic polymers. The copolymers of vinyl pyrrolidone are also usable according to the invention, such as the commercially available products Copolymer 845 (manufacturer: ISP), Gaffix® VC 713 (manufacturer: ISP), Gafquat® ASCP 1011, Gafquat®HS 110, Luviquat® 8155 and Luviquat® MS 370.

Further suitable cationic polymers according to the invention are the "temporarily cationic" polymers. These polymers usually comprise an amino group that is present at specific pH values as the quaternary ammonium group and is thus cationic. Chitosan and its derivatives, such as for example the commercially available Hydagen® CMF, Hydagen® HCMF, Kytamer® PC and Chitolam® NB/101 are preferred.

Inventively preferred cationic polymers are cationic cellulose derivatives and chitosan and its derivatives, particularly the commercial products Polymer® JR 400, Hydagen® HCMF and Kytamer® PC, cationic guar derivatives, cationic honey derivatives such as the commercial product Honeyquat® 50, cationic alkyl polyglycosides according to DE-PS 44 13 686 and quaternary nitrogen polymers of the type Polyquaternium-37.

In addition, cationized protein hydrolyzates are considered as cationic polymers, wherein the base protein hydrolyzate can originate from animals (e.g., from collagen, milk or keratin), from plants (e.g., from wheat, maize, rice, potatoes, soya or almonds), from marine life (e.g., from fish collagen or algae), or from biotechnologically obtained protein hydrolyzates.

Cationic protein hydrolyzates and derivatives based on plants are particularly preferred.

Preferably employed amphoteric polymers include polymers composed from—
(a) monomers of quaternary ammonium groups of the general Formula (G1-II),

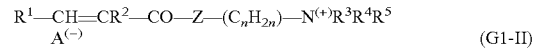

(G1-II)

wherein $R^1$ and $R^2$ are each independently hydrogen or a methyl group; $R^3$, $R^4$ and $R^5$ are each independently alkyl groups having 1 to 4 carbon atoms; Z is an NH-group or an oxygen atom; n is a whole number from 2 to 5; and $A^{(-)}$ is the anion of an organic or inorganic acid, and
(b) monomers of carboxylic acids of the general Formula (G1-III),

(G1-III)

wherein $R^6$ and $R^7$ are each independently hydrogen or a methyl group.

According to the invention, these compounds can be added directly as well as in their salt form, the latter obtained, for example, by neutralization of the polymer with an alkali hydroxide. Quite particularly preferred are polymers that incorporate type (a) monomers wherein $R^3$, $R^4$ and $R^5$ are methyl groups, Z is an NH-group and $A^{(-)}$ is a halide, methoxysulfate or ethoxysulfate ion. Acrylamido propyltrimethylammonium chloride is a particularly preferred monomer (a). Acrylic acid is preferably used as monomer (b) in the cited polymers.

Inventive agents preferably comprise conditioning, cationic and/or amphoteric polymers in a quantity of about 0.01 to about 5 wt. %, particularly in a quantity of about 0.1 to about 2 wt. %, based on total weight of the end-use preparation.

Agents according to the invention can further comprise at least one vitamin, one provitamin, one vitamin precursor and/or one of their derivatives as the conditioner.

According to the invention, those vitamins, provitamins and vitamin precursors are preferred which are normally classified in the groups A, B, C, E, F and H.

Agents according to the invention preferably comprise vitamins, provitamins and vitamin precursors from groups A, B, C, E and H. Panthenol, pantolactone, pyridoxine and its derivatives, as well as nicotinamide and biotin are especially preferred. D-panthenol is particularly preferably employed as a conditioner, optionally in combination with at least one of the abovementioned silicone derivatives.

Agents according to the invention can further comprise at least one plant extract as a conditioner. Usually, these extracts are manufactured by extraction of the whole plant. In individual cases, however, the extracts can be produced solely from blossoms and/or leaves of the plant. According to the invention, extracts from green tea, oak bark, stinging nettle, hamamelis, hops, henna, camomile, burdock root, field horsetail, hawthorn, linden flowers, almonds, aloe vera, spruce needles, horse chestnut, sandal wood, juniper, coconut, mango, apricot, lime, wheat, kiwi, melon, orange, grapefruit, sage, rosemary, birch, malva, lady's smock, common yarrow, thyme, lemon balm, rest-harrow, coltsfoot, marshmallow (althaea), meristem, ginseng and ginger are preferred.

Extracts from green tea, oak bark, stinging nettle, hamamelis, hops, camomile, burdock root, hawthorn, linden flowers, almonds, aloe vera, coconut, mango, apricot, lime, wheat, kiwi, melon, orange, grapefruit, sage, rosemary, birch, lady's smock, common yarrow, rest-harrow, meristem, ginseng and ginger are particularly preferred.

Extracts of green tea, almonds, *aloe vera*, coconut, mango, apricot, lime, wheat, kiwi and melon are quite particularly suitable. The extraction agent used to prepare the cited plant extracts can be water, alcohols as well as their mixtures. Exemplary preferred alcohols are lower alcohols such as ethanol and isopropanol, but particularly polyhydroxy alcohols such as ethylene glycol, propylene glycol and butylene glycol, both as the sole extracting agent as well as in aqueous mixtures. Plant extracts based on water/propylene glycol in the ratio 1:10 to 10:1 have proven particularly suitable. According to the invention, the plant extracts can be used in pure and also in diluted form. When they are used in diluted form, they normally comprise ca. 2-80 wt. % active substance and the solvent is the extracting agent or mixture of extracting agents used for their preparation. In addition, it can be preferred to employ mixtures of a plurality, particularly two different plant extracts in the agents according to the invention.

A series of carboxylic acids is also suitable as the conditioner.

Moreover, according to the invention it is preferred to utilize 2-pyrrolidinone-5-carboxylic acid and its derivatives as the carboxylic acid. Sodium, potassium, calcium, magnesium or ammonium salts are particularly preferred wherein the ammonium ion carries one to three $C_1$- to $C_4$ alkyl groups besides hydrogen. The sodium salt is quite particularly preferred. Quantities utilized in products according to the invention are preferably about 0.05 to about 10 wt. %, based on the total preparation, particularly preferably about 0.1 to about 5 wt. %, and especially preferably about 0.1 to about 3 wt. %.

In addition, it is preferred to add hydroxycarboxylic acids—here once again the dihydroxy-, trihydroxy- and polyhydroxy carboxylic acids, as well as the dihydroxy-, trihydroxy- and polyhydroxy di-, tri- and polycarboxylic acids. In this respect, it was shown that besides the hydroxycarboxylic acids, also the hydroxycarboxylic acid esters as well as mixtures of hydroxycarboxylic acids and their esters and also polymeric hydroxycarboxylic acids and their esters can be quite particularly preferred. Preferred hydroxycarboxylic acid esters are fully esterified glycolic acid, lactic acid, malic acid, tartaric acid or citric acid, for example. Additional fundamentally suitable hydroxycarboxylic acid esters are esters of β-hydroxypropionic acid, of tartronic acid, of D-gluconic acid, of saccharic acid, of mucic acid or of glucuronic acid. Primary, linear or branched aliphatic alcohols containing 8-22 carbon atoms, i.e. fatty alcohols or synthetic fatty alcohols, are suitable alcohol units of these esters. The esters of $C_{12}$-$C_{15}$ fatty alcohols are particularly preferred in this respect. Esters of this type are commercially available, for example, under the trade name Cosmacol® from Enichem, Augusta Industriale. Particularly preferred polyhydroxypolycarboxylic acids are polylactic acid and polytartaric acid as well as their esters.

Ectoin or ectoin derivatives, allantoin, taurine and/or bisabolol are also suitable conditioners.

Mono- or oligosaccharides can also be incorporated as the conditioner into the agents according to the invention. Both monosaccharides as well as oligosaccharides, such as for example raw sugar, lactose and raffinose can be incorporated. According to the invention, the use of monosaccharides is preferred. Once again, the monosaccharides preferably include those compounds that contain 5 or 6 carbon atoms.

Inventive agents preferably comprise mono- or oligosaccharides in an amount of 0.1 to 8 wt. %, particularly preferably 1 to 5 wt. %, based on total end-use preparation.

The agent can further comprise at least one lipid as a conditioner.

According to the invention, suitable lipids are phospholipids, for example soy lecithin, egg lecithin and cephalin, as well as substances known under the INCI names Linoleamidopropyl PG-Dimonium Chloride Phosphate, Cocamidopropyl PG-Dimonium Chloride Phosphate and Stearamidopropyl PG-Dimonium Chloride Phosphate. These are commercialized, for example, by the Mona Company under the trade names Phospholipid EPA®, Phospholipid PTC® and Phospholipid SV®.

Agents according to the invention preferably comprise lipids in amounts of 0.01 to 10 wt. %, in particular 0.1 to 5 wt. %, based on total end-use preparation.

Oil bodies are also suitable as a conditioner. Natural and synthetic cosmetic oil bodies include— vegetable oils. Examples of such oils are sunflower oil, olive oil, soya oil, rapeseed oil, almond oil, jojoba oil, orange oil, wheat germ oil, peach stone oil and the liquid parts of coconut oil. Other triglyceride oils such as the liquid fractions of beef tallow as well as synthetic triglyceride oils are also suitable.

liquid paraffin oils, isoparaffin oils and synthetic hydrocarbons as well as di-n-alkyl ethers containing a total of 12 to 36 carbon atoms, particularly 12 to 24 carbon atoms such as di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether and di-tert.butyl ether, diisopentyl ether, di-3-ethyldecyl ether, tert.butyl n-octyl ether, isopentyl n-octyl ether and 2-methylpentyl n-octyl ether. The commercial products 1,3-di-(2-ethylhexyl)cyclohexane (Cetiol® S) and di-n-octyl ether (Cetiol® OE) can be preferred.

Ester oils. Ester oils refer to the esters of $C_6$-$C_{30}$ fatty acids with $C_2$-$C_{30}$ fatty alcohols. Monoesters of fatty acids with alcohols having 2 to 24 carbon atoms are preferred. Examples of fatty acids units utilized in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures, that result, for example, from cracking of natural fats and oils, from the oxidation of aldehydes, from Roelen's Oxo Synthesis, or from the dimerization of unsaturated fatty acids. Examples for the fatty alcohol units in the ester oils are isopropyl alcohol, caproyl alcohol, capryl alcohol, 2-ethylhexyl alcohol, 1-decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol as well as their technical mixtures, that, for example, result from the high pressure hydrogenation of industrial methyl esters based on fats and oils or aldehydes from Roelen's oxo synthesis as well as the monomer fraction on the dimerization of unsaturated fatty alcohols. According to the invention, isopropyl myristate (Rilanit® IPM), isononanoic acid C16-18 alkyl ester (Cetiol® SN), 2-ethylhexyl palmitate (Cegesoft® 24), Stearic acid 2-ethylhexyl ester (Cetiol® 868), Cetyl oleate, glycerine tricaprylate, cocofatty alcohol caprinate/-caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are particularly preferred.

Dicarboxylic acid esters such as di-n-butyl adipate, di-(2-ethylhexyl) adipate, di-(2-ethylhexyl) succinate and di-isotridecyl acetate as well as diol esters such as ethylene glycol dioleate, ethylene glycol di-isotridecanoate, propylene glycol di(2-ethylhexanoate), propylene glycol di-isostearate, propylene glycol di-pelargonate, butanediol di-isostearate, neopentyl glycol dicaprylate, symmetrical, unsymmetrical or cyclic esters of carbon dioxide with fatty alcohols (e.g., as described in DE-OS197 56 454), glycerine carbonate or dicaprylyl carbonate (Cetiol® CC), trifatty acid esters of saturated and/or unsaturated linear and/or branched fatty acids with glycerine, fatty acid partial glycerides, under which are understood monoglycerides, diglycerides and their industrial mixtures. When using industrial products, minor amounts of triglycerides may still be contained as a result of the production process. The partial glycerides preferably comply with the Formula (D4-I)—

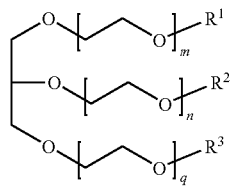

wherein $R^1$, $R^2$ and $R^3$ are independently hydrogen or a linear or branched, saturated and/or unsaturated acyl group with 6 to 22 carbon atoms, preferably 12 to 18 carbon atoms, with the proviso that at least one of these groups stands for an acyl group and at least one of these groups stands for hydrogen. The sum of (m+n+q) is 0 or numbers from 1 to 100, preferably 0 or 5 to 25. Preferably, $R^1$ is an acyl group, $R^2$ and $R^3$ are hydrogen, and the sum of (m+n+q) is 0. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures. Oleic acid monoglycerides are preferably employed.

The added quantity of natural and synthetic cosmetic oil bodies in agents according to the invention is usually 0.1 to 30 wt. %, based on total end-use preparation, preferably 0.1 to 20 wt. % and particularly 0.1 to 15 wt. %.

Moreover, the agent can comprise an enzyme as a conditioner. According to the invention, particularly preferred enzymes are chosen from proteases, lipases, transglutaminases, oxidases and peroxidases.

Although each of the cited conditioners alone already provides a satisfactory result, in the context of the present invention all embodiments are included in which the agent comprises a plurality of conditioners, even from different groups.

By adding a UV filter, the agent itself as well as the treated skin or hair can be protected against damage from UV radiation. Consequently, at least one UV filter is preferably added to the agent. Suitable UV filters are not generally limited in regard to structure and physical properties. Indeed, all UV filters employed in the cosmetic field having an absorption maximum in the UVA (315-400 nm), in the UVB (280-315 nm) or in the UVC (<280 nm) regions are suitable. UV filters having an absorption maximum in the UVB region, especially in the range from about 280 to about 300 nm, are particularly preferred.

Inventively preferred UV-filters are chosen from substituted benzophenones, p-aminobenzoates, diphenylacrylates, cinnamates, salicylates, benzimidazoles and o-aminobenzoates.

The agent preferably comprises UV filters in quantities of 0.01 to 5 wt. %, based on total end-use preparation. Quantities of 0.1 to 2.5 wt. % are preferred.

Depending on the type of the agent according to the invention, it may be necessary for them to comprise at least one surfactant. This is particularly true for skin cleansers and shampoos. However, other agents such as hair rinses, hair tonics and certain styling agents, especially styling foams, can also comprise surfactants.

For example, cationic surfactants as described above can be added as suitable conditioners. The above descriptions are also valid in regard to preferred cationic surfactants and their added quantities.

In addition to or instead of cationic surfactants, the agents can comprise further surfactants or emulsifiers, wherein anionic as well as ampholytic and non-ionic surfactants and all types of known emulsifiers are suitable. Ampholytic or amphoteric surfactants include zwitterionic surfactants and ampholytes. The surfactants can already have an emulsifying action.

Suitable anionic surfactants include all anionic surface-active materials suitable for use on the human body. They are characterized by a water solubilizing anionic group such as a carboxylate, sulfate, sulfonate or phosphate group, and a lipophilic alkyl group containing about 8 to 30 carbon atoms. In addition, the molecule may comprise glycol or polyglycol ether groups, ester, ether and amide groups as well as hydroxyl groups. Exemplary suitable anionic surfactants are each in the form of the sodium, potassium and ammonium as well as the mono, di and trialkanolammonium salts containing 2 to 4 carbon atoms in the alkanol group

- linear and branched fatty acids with 8 to 30 carbon atoms (soaps),
- ether carboxylic acids of the formula R—O—($CH_2$—$CH_2O$)$_x$—$CH_2$—COOH, in which R is a
- linear alkyl group containing 8 to 30 carbon atoms and x=0 or 1 to 16,
- acyl sarcosides with 8 to 24 carbon atoms in the acyl group,
- acyl taurides with 8 to 24 carbon atoms in the acyl group,
- acyl isethionates with 8 to 24 carbon atoms in the acyl group,
- mono- and dialkyl esters of sulfosuccinic acid with 8 to 24 carbon atoms in the alkyl group and mono-alkyl polyoxyethyl esters of sulfosuccinic acid with 8 to 24 carbon atoms in the alkyl group and 1 to 6 oxyethylene groups,
- linear alkane sulfonates containing 8 to 24 carbon atoms,
- linear alpha-olefin sulfonates containing 8 to 24 carbon atoms,
- alpha-sulfo fatty acid methyl esters of fatty acids containing 8 to 30 carbon atoms,
- alkyl sulfates and alkyl polyglycol ether sulfates of formula R—O($CH_2$—$CH_2O$)$_x$—$OSO_3H$, in which R is preferably a linear alkyl group containing 8 to 30 carbon atoms and x=0 or 1 to 12,
- mixtures of surface-active hydroxysulfonates,
- sulfated hydroxyalkyl polyethylene glycol ethers and/or hydroxyalkylene propylene glycol ethers,
- sulfonated unsaturated fatty acids with 8 to 24 carbon atoms and 1 to 6 double bonds,
- esters of tartaric acid and citric acid with alcohols, which represent the addition products of about 2-15 molecules of ethylene oxide and/or propylene oxide on fatty alcohols containing 8 to 22 carbon atoms,
- alkyl- and/or alkenyl ether phosphates of Formula (E1-I),

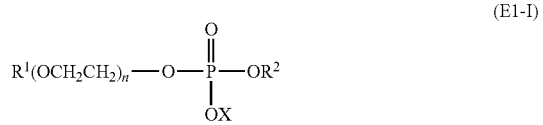

(E1-I)

wherein $R^1$ preferably is an aliphatic hydrocarbon group containing 8 to 30 carbon atoms; $R^2$ is hydrogen, a $(CH_2CH_2O)_n R^1$ group or X, n is a number from 1 to 10, and X is hydrogen, an alkali- or alkaline earth metal or $NR^3R^4R^5R^6$, with $R^3$ to $R^6$ are each independently a $C_1$ to $C_4$ hydrocarbon group, sulfated fatty acid alkylene glycol esters of Formula (E1-II)

(E1-II)

wherein $R^7CO$— is a linear or branched, aliphatic, saturated and/or unsaturated acyl group containing 6 to 22 carbon atoms; Alk is $CH_2CH_2$, $CHCH_3CH_2$ and/or $CH_2CHCH_3$; n is a number from 0.5 to 5; and M is a cation, such as described in DE-OS197 36 906, monoglyceride sulfates and monoglyceride ether sulfates of Formula (E1-III)

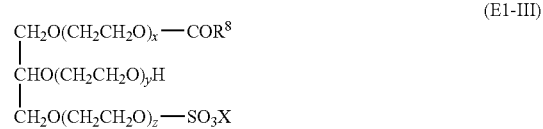

(E1-III)

wherein $R^8CO$ is a linear or branched acyl group containing 6 to 22 carbon atoms; the sum of x, y and z is 0 or a number from 1 to 30, preferably 2 to 10; and X is an alkali metal or alkaline earth metal. In the context of the invention, typical examples of suitable monoglyceride (ether) sulfates are the reaction products of lauric acid monoglyceride, cocoa fatty acid monoglyceride, palmitic acid monoglyceride, stearic acid monoglyceride, oleic acid monoglyceride and tallow fatty acid monoglyceride as well as their ethylene oxide adducts with sulfur trioxide or chlorosulfonic acid in the form of their sodium salts. Preferably, monoglyceride sulfates of Formula (E1-III) are added, in which $R^8CO$ is a linear acyl group containing 8 to 18 carbon atoms, amido ether carboxylic acids, and condensation products of $C_8$-$C_{30}$ fatty alcohols with protein hydrolyzates and/or amino acids and their derivatives, known to the person skilled in the art as albumin fatty acid condensates, such as the Lamepon® types, Gluadin® types, Hostapon® KCG or the Amisoft® types.

Preferred anionic surfactants include alkyl sulfates, alkyl polyglycol ether sulfates and ether carboxylic acids with 10 to 18 carbon atoms in the alkyl group and up to 12 glycol ether groups in the molecule, sulfosuccinic acid mono and dialkyl esters with 8 to 18 C atoms in the alkyl group and sulfosuccinic acid mono-alkyl polyoxyethyl esters with 8 to 18 C atoms in the alkyl group and 1 to 6 oxyethylene groups, monoglycerine disulfates, alkyl- and alkenyl ether phosphates as well as albumin fatty acid condensates.

Zwitterionic surfactants refer to those surface-active compounds having at least one quaternary ammonium group and at least one —$COO^{(-)}$ or $SO_3^{(-)}$ group in the molecule. Particularly suitable zwitterionic surfactants are betaines such as N-alkyl-N,N-dimethylammonium glycinates, for example, cocoalkyl dimethylammonium glycinate, N-acylaminopropyl-N,N-dimethylammonium glycinates, for example, cocoacylaminopropyl dimethylammonium glycinate, and 2-alkyl-3-carboxymethyl-3-hydroxyethyl imidazolines with 8 to 18 carbon atoms in each of the alkyl or acyl groups, as well as cocoacylaminoethyl hydroxyethyl carboxymethyl glycinate. A preferred zwitterionic surfactant is the fatty acid amide derivative known under the INCI name Cocamidopropyl Betaine.

Ampholytes include such surface-active compounds that apart from a $C_{8-24}$ alkyl or acyl group, comprise at least one free amino group and at least one —COOH or —$SO_3H$ group in the molecule and are able to form internal salts. Examples of suitable ampholytes are N-alkylglycines, N-alkyl propionic acids, N-alkylamino butyric acids, N-alkylimino dipropionic acids, N-hydroxyethyl-N-alkylamidopropylglycine, N-alkyltaurines, N-alkylsarcosines, 2-alkylamino propionic acids and alkylamino acetic acids, each with about 8 to 24 carbon atoms in the alkyl group. Particularly preferred ampholytes are N-cocoalkylamino propionate, cocoacylaminoethylamino propionate and $C_{12}$-$C_{18}$ acyl sarcosine.

Non-ionic surfactants comprise, for example, a polyol group, a polyalkylene glycol ether group or a combination of polyol ether groups and polyglycol ether groups as the hydrophilic group. Exemplary compounds of this type include—

- addition products of 2 to 50 moles ethylene oxide and/or 1 to 5 moles propylene oxide to linear and branched fatty alcohols containing 8 to 30 carbon atoms, to fatty acids containing 8 to 30 carbon atoms and to alkyl phenols containing 8 to 15 carbon atoms in the alkyl group,
- methyl or $C_2$-$C_6$ alkyl group end blocked addition products of 2 to 50 moles ethylene oxide and/or 1 to 5 moles propylene oxide to linear and branched fatty alcohols with 8 to 30 carbon atoms, to fatty acids with 8 to 30 carbon atoms and to alkyl phenols with 8 to 15 carbon atoms in the alkyl group, such as, for example, the commercially available types Dehydol® LS, Dehydol® LT (Cognis),
- $C_{12}$-$C_{30}$ fatty acid mono- and diesters of addition products of 1 to 30 moles ethylene oxide to glycerine,
- addition products of 5 to 60 moles ethylene oxide on castor oil and hydrogenated castor oil,
- polyol esters of fatty acids, such as, for example, the commercial product Hydagen® HSP (Cognis) or Sovermol types (Cognis),
- alkoxylated triglycerides,
- alkoxylated fatty acid alkyl esters of the formula (E4-I)

$$R^1CO\text{—}(OCH_2CHR^2)_wOR^3 \qquad (E4\text{-}I)$$

wherein $R^1CO$ is a linear or branched, saturated and/or unsaturated acyl group containing 6 to 22 carbon atoms; $R^2$ is hydrogen or methyl; $R^3$ is linear or branched alkyl groups containing 1 to 4 carbon atoms; and x is a number from 1 to 20,
- amine oxides,
- mixed hydroxy ethers, such as are described for example in DE-OS1 973 8866,
- sorbitol esters of fatty acids and addition products of ethylene oxide to sorbitol esters of fatty acids such as the polysorbates,
- sugar esters of fatty acids and addition products of ethylene oxide to sugar esters of fatty acids,
- addition products of ethylene oxide to fatty acid alkanolamides and fatty amines,
- sugar surfactants of the type alkyl and alkenyl oligoglycosides according to Formula (E4-II),

$$R^4O\text{-}[G]_p \qquad (E4\text{-}II)$$

wherein $R^4$ is an alkyl or alkenyl group containing 4 to 22 carbon atoms; G is a sugar group containing 5 or 6 carbon atoms; and p is a number from 1 to 10. Preferably, alkyl and/or alkenyl oligoglycosides are employed with an average degree of oligomerization p of 1.1 to 3.0. Alkyl oligoglucosides with chain lengths $C_8$-$C_{10}$ (DP=1 to 3) are preferred, which result as the low boiling fraction in the separative distillation of industrial $C_8$-$C_{18}$ coco fatty alcohol and which can be contaminated with a fraction of less than 6 wt. % of $C_{12}$ alcohol, as well as alkyl oligoglucosides based on industrial $C_{9/11}$ oxo alcohols (DP=1 to 3). The alkyl or alkenyl group $R^{15}$ can moreover be derived from primary alcohols containing 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as their industrial mixtures that can be obtained as described above. Alkyl oligoglucosides based on hydrogenated $C_{12/14}$ coco alcohol with a DP of 1 to 3 are preferred.

Alkylene oxide addition products to saturated, linear fatty alcohols and fatty acids, each with 2 to 30 moles ethylene oxide per mole fatty alcohol or fatty acid, are preferred non-ionic surfactants. Preparations with excellent properties are also obtained when they comprise fatty acid esters of ethoxylated glycerine as the non-ionic surfactant.

These compounds are characterized by the following parameters. The alkyl group R comprises 6 to 22 carbon atoms and may be both linear and also branched. Primary linear aliphatic groups and aliphatic groups that are methyl-branched in the 2-position are preferred. Such alkyl groups are for example 1-octyl, 1-decyl, 1-lauryl, 1-myristyl, 1-cetyl and 1-stearyl. 1-Octyl, 1-decyl, 1-lauryl, 1-myristyl are particularly preferred. On using so-called "oxo alcohols" as starting materials, compounds with an odd number of carbon atoms in the alkyl chain preponderate.

Sugar surfactants can also be used as non-ionic surfactants. They are preferably present in amounts of 0.1 to 20 wt. %, based on total agent. Quantities of 0.5 to 15 wt. % are particularly preferred, and quantities of 0.5 to 7.5 wt. % are quite particularly preferred.

For compounds with alkyl groups that are used as surfactants, they may each be pure substances. However, it is normally preferred to start with natural vegetal or animal raw materials for the manufacture of these materials, with the result that mixtures of substances are obtained which have different alkyl chain lengths that depend on each raw material.

For surfactants represented by the addition products of ethylene oxide and/or propylene oxide to fatty alcohols or derivatives of these addition products, products with a "normal" homolog distribution as well as those with a narrow homolog distribution may be used. The term "normal" homolog distribution refers to mixtures of homologs obtained from the reaction of fatty alcohols and alkylene oxide using alkali metals, alkali metal hydroxides or alkali metal alcoholates as catalysts. Narrow homolog distributions are obtained if e.g. hydrotalcite, alkaline earth metal salts of ether carboxylic acids, alkaline earth metal oxides, hydroxides or alcoholates are used as catalysts. The use of products with a narrow homolog distribution can be preferred.

The additional surfactants are generally added in quantities of 0.1-45 wt. %, preferably 0.5-30 wt. % and quite particularly preferably from 0.5-25 wt. %, based on the total agent. The added quantity depends essentially on the purpose the inventive agent. For a shampoo or another cleansing agent, surfactant levels above 45 wt. % are also typical.

The agents can additionally comprise at least one emulsifier. Emulsifiers act at the interface to produce water or oil-stable adsorption layers that protect the dispersed droplets against coalescence and thereby stabilize the emulsion. Thus, emulsifiers, like surfactants are composed of hydrophobic and hydrophilic molar units. Hydrophilic emulsifiers preferably form O/W emulsions and hydrophobic emulsifiers preferably form W/O emulsions. The choice of this emulsifying surfactant or emulsifier depends on the materials being dispersed and the respective external phase as well as the fineness of the emulsion. Exemplary emulsifiers usable according to the invention include—

- addition products of 4 to 100 moles ethylene oxide and/or 1 to 5 moles propylene oxide to linear fatty alcohols containing 8 to 22 carbon atoms, to fatty acids containing 12 to 22 carbon atoms and to alkyl phenols containing 8 to 15 carbon atoms in the alkyl group;
- $C_{12}$-$C_{22}$ fatty acid mono- and diesters of addition products of 1 to 30 moles ethylene oxide on polyols containing 3 to 6 carbon atoms, especially glycerine;

ethylene oxide and polyglycerine addition products on methyl glucoside fatty acid esters, fatty acid alkanolamides and fatty acid glucamides;

$C_8$-$C_{22}$ alkyl mono and oligoglycosides and their ethoxylated analogs, wherein the degrees of oligomerization are 1.1 to 5, particularly 1.2 to 2.0 and glucose as the sugar component are preferred;

mixtures of alkyl(oligo) glucosides and fatty alcohols, for example the commercially available product Montanov® 68;

addition products of 5 to 60 moles ethylene oxide on castor oil and hydrogenated castor oil;

partial esters of polyols containing 3-6 carbon atoms with saturated fatty acids containing 8 to 22 carbon atoms;

sterols. Sterols are understood to mean a group of steroids, which carry a hydroxyl group on carbon atom 3 of the steroid skeleton and are isolated from both animal tissue (zoosterols) and vegetal fats (phytosterols). Examples of zoosterols are cholesterol and lanosterol. Examples of suitable phytosterols are ergosterol, stigmasterol and sitosterol. Sterols, the so-called mycosterols, are also isolated from fungi and yeasts.

phospholipids. Among these are principally meant the glucose phospholipids, which are obtained e.g. as lecithins or phosphatidyl cholines from e.g. egg yolk or plant seeds (e.g. soya beans).

fatty acid esters of sugars and sugar alcohols such as sorbitol;

polyglycerines and polyglycerine derivatives such as for example polyglycerine poly-12-hydroxystearate (commercial product Dehymuls® PGPH), linear and branched fatty acids containing 8 to 30 carbon atoms and their Na, K, ammonium, Ca, Mg and Zn salts.

The emulsifiers are preferably added in amounts of 0.1 to 25 wt. %, especially 0.1 to 3 wt. %, based on the total agent.

In addition to the cited components, the agents can furthermore comprise all active substances, additives and auxiliaries known for such cosmetics.

Further exemplary active products, auxiliaries and additives include— thickeners such as agar-agar, guar gum, alginates, xanthane gum, gum arabica, karaya gum, locust bean flour, linseed gums, dextrans, cellulose derivatives, e.g. methyl cellulose, hydroxyalkyl cellulose and carboxymethyl cellulose, starch fractions and derivatives such as amylose, amylopectin and dextrins, clays such as e.g. bentonite, synthetic hydrocolloids such as e.g. polyvinyl alcohol, and optionally crosslinked polyacrylates, silicates (e.g. Laponite® XLG), gel-forming thickeners (z.B. Structure® 2001, Synthylen® 2000);

structurants such as maleic acid and lactic acid;

perfume oils, dimethyl isosorbitol and cyclodextrins;

solvents and solubilizers such as ethanol, isopropanol, ethylene glycol, propylene glycol, glycerine and diethylene glycol;

quaternized amines, such as methyl 1-alkylamidoethyl-2-alkylimidazolium methosulfate;

defoamers such as silicones;

dyestuffs to color the agent;

anti-dandruff active materials such as Piroctone Olamine, zinc Omadine and Climbazole;

substances for adjusting the pH, such as, for example, customary acids, in particular food acids, and bases;

cholesterol;

texturizers such as sugar esters, polyol esters or polyol alkyl ethers;

fats and waxes such as spermaceti, beeswax, montan wax and paraffins;

fatty acid alkanolamides;

chelating agents such as EDTA, NTA, β-alanine diacetic acid and phosphonic acids;

swelling and penetration agents such as glycerine, propylene glycol monoethyl ether, carbonates, hydrogen carbonates, guanidines, ureas, and primary, secondary and tertiary phosphates;

opacifiers such as latex, styrene/PVP copolymers and styrene/acrylamide copolymers;

pearlizing agents, such as ethylene glycol mono- and distearate as well as PEG-3 distearate;

preservatives;

stabilizers for hydrogen peroxide and other oxidizing agents;

propellants such as propane-butane mixtures, $N_2O$, dimethyl ether, $CO_2$ and air; and antioxidants.

With regard to further optional ingredients and their amounts used, reference is expressly made to the relevant handbooks known to the person skilled in the art.

The formulation of the inventive agents can be in all usual cosmetic forms, for example, in the form of solutions that can be applied as facial or hair water or pump or aerosol spray onto the skin or hair, in the form of creams, emulsions, waxes, gels or also surfactant-containing foaming solutions or other preparations, which are suitable for application on the skin or the hair.

However, the inventive agents preferably concern agents for the temporary shaping of keratin-containing fibers, i.e. styling agents. Preferred styling agents are styling gels, pump hair sprays, aerosol hair sprays, pump hair foams and aerosol hair foams.

In the context of the present application, "styling gels" is the generic term for clear or turbid products, styling waxes, styling creams, styling lotions, styling jellys, etc. Finally, all agents for hairdressing which are not hair sprays or foams fall under this term.

Hair foams are understood in this regard to mean agents that form foam when removed from a suitable container. It may be required to add ingredients to the agent which promote foaming or which stabilize initially formed foam. Surfactants and/or emulsifiers are particularly suitable for this, as has been described previously. Preferably, surfactants from the group of the cationic surfactants are utilized.

Hair creams and hair gels generally comprise structurants and/or thickening polymers, which lend the desired consistency to the products. Structurants and/or thickening polymers are typically added in amounts of 0.1 to 10 wt. %, based on the total product. Quantities of 0.5 to 5 wt. %, particularly 0.5 to 3 wt. %, are preferred. However, as the inventively added polymer combination possesses self-thickening properties, the addition of additional structurants and/or thickening polymers is not absolutely necessary. The inventive agents preferably comprise no additional structurants and/or thickening polymers.

When the inventive agents concern an aerosol product then this imperatively comprises a propellant.

Inventively suitable exemplary propellants are $N_2O$, dimethyl ether, $CO_2$, air and alkynes containing 3 to 5 carbon atoms, such as propane, n-butane, iso-butane, n-pentane and iso-pentane, and their mixtures. Dimethyl ether, propane, n-butane, iso-butane and their mixtures are preferred.

The cited alkanes, mixtures of the cited alkanes or mixtures of the cited alkanes with dimethyl ether are preferred as the sole propellant. However, the invention also explicitly includes the joint utilization with propellants of the fluorochlorohydrocarbon type, but especially fluorinated hydrocarbons.

In regard to the weight ratio of propellant to the usual ingredients of the preparation, the size of the aerosol droplets or the foam bubbles and the relevant size distribution can be adjusted for a given spray device.

The quantity of added propellant varies as a function of the actual agent of the agent, the packaging used and the desired product type, for example hair spray or hair foam. When a conventional spray device is used, aerosol foam products preferably comprise the propellant in amounts of 1 to 35 wt. %, based on the total product. Quantities of 2 to 30 wt. %, especially 3 to 15 wt. %, are particularly preferred. Aerosol sprays generally comprise greater amounts of propellant. In this case the propellant is preferably added in amounts of 30 to 98 wt. %, based on the total product. Quantities of 40 to 95 wt. %, especially 50 to 95 wt. %, are particularly preferred.

The aerosol products can be manufactured according to conventional techniques. Generally, all ingredients of the agent, excepting the propellant, are charged into a suitable pressure-resistant container. This is thereupon sealed with a valve. The desired quantity of propellant is then filled by means of conventional techniques.

Accordingly, a second subject matter of the invention is a process in which the inventive, cosmetic agent is applied onto the hair as a pump hair spray, aerosol hair spray, pump hair foam, aerosol hair foam or styling gel and is optionally worked into the hair with the palms of the hand and/or the fingers.

The desired shaping of the hair can then be carried out with the fingers or hands as well as with suitable conventional aids such as for example a comb or brush.

A third subject matter of the invention is the use of the inventive agent for the temporary shaping of keratin-containing fibers.

The inventive agents and products that comprise these agents are particularly characterized in that they lend the treated hair a very strong and moisture resistant hair set.

Another subject matter of the present invention is a process in which the inventive, cosmetic agent is applied onto the hair as a pump hair spray, aerosol hair spray, pump hair foam, aerosol hair foam, or styling gel, and is optionally worked into the hair with the palms of the hand and/or the fingers.

The statements made for the inventive agents are valid mutatis mutandis for the inventive process.

A further subject matter of the present invention is the use of polymer mixtures comprising— a) at least one copolymer A comprising
at least one structural unit according to Formula (I)

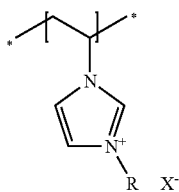

(I)

wherein
R is a $C_1$ to $C_{30}$ alkyl group, a $C_1$ to $C_4$ aralkyl group, a $C_2$ to $C_6$ alkenyl group or a $C_2$ to $C_6$ hydroxyalkyl group, and
$X^-$ is a physiologically compatible anion;

and at least one further structural unit according to Formula (II)

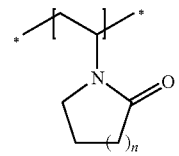

(II)

wherein n is 1, 2 or 3 as the number of methylene units
b) and at least one acrylate polymer B different from copolymer A and chosen from
b1) polyacrylic acid and/or
b2) copolymers of methacrylic acid with acrylamido propane sulfonic acid and/or
b3) copolymers of acrylic acid with methacrylic acid and acrylic acid esters and/or
b4) copolymers of acrylic acid with methacrylic acid with acrylic acid esters and methacrylic acid esters and/or
b5) copolymers of acrylic acid with methacrylic acid esters for improving the hold of the hairstyle, particularly in increased ambient humidity.

The statements made for the inventive agents are also valid mutatis mutandis for the inventive process.

In the context of the present invention, the hold of the style, also called hairstyle set, together with flexibility, elasticity and plasticity, are determined by the Omega-Loop method.

For this, a dry tress of hair (Euro-Naturhaar from the Kerling Company, adhesive tress compacted, adhesive on one side, total length 150 mm, free length 130 mm, width 10 mm, weight 0.9±0.1 g) was dipped for 30 seconds up to the lower edge of the mask into the test polymer solution. The excess solution was then wiped off between thumb and index finger, such that there remained 0.5±0.02 g of the solution on the hair. The tress of hair that was saturated with the test solution was wrapped round a Teflon cylinder with a diameter of 36 mm, and the projecting ends were fixed with a clip. The prepared tresses were then dried and conditioned overnight in the climatic test cabinet at 25° C. and 50% relative humidity or at 25° C. and 75% relative humidity.

The conditioned tress was carefully removed from the Teflon cylinder. The resulting Ω-Loop, a circular structure of the hair, stabilized in its shape by the formed polymer film, was clamped in the gripper attached to the load cell and lowered close above the base plate of a universal testing machine AMETEK LF Plus from AMETEK Precision Instruments Europe GmbH, Product group Lloyd. The complete measurement is carried out in the climatic test cabinet under constant climatic conditions at 25° C. and 50% relative humidity or at 25° C. and 75% relative humidity.

In order to create standardized starting conditions, the measurement begins with the start up of an initial load of 0.07 N with a speed of 30 mm min$^{-1}$. The Ω-Loop was then compressed by 8 mm with a speed of 60 mm min$^{-1}$, the required force for this being measured. Once the characteristic force $F_1$ at the maximum deformation of 8 mm had been recorded, the strain on the tress was relieved at 60 mm min$^{-1}$ so far that the tress lifts 10 mm from the base plate. From this point on begins the next cycle, in that the initial load of 0.07 N is initialized and the tress is then compressed by 8 mm, the same speeds being used as described above. The measurement of an Ω-Loop includes a total of 10 cycles.

Four characteristic parameters are determined by this measurement technique to describe the mechanical properties of film forming polymers. Using the following formulae, hold, flexibility, plasticity and elasticity can be calculated from the measured forces—

Hold=$F_1$[N]

($F_1$ corresponds to the maximum force of the measurement)

$$\text{Flexibility} = \frac{F_{10}}{F_1}$$

(represents the ratio of the maximum force of the tenth to the first cycle)

$$\text{Plasticity} = \frac{2 \cdot H_1 - H_{10}}{H_1}$$

(with $H_1$=9 mm and $H_{10}$=9 mm+permanent plastic deformation of the stress)

$$\text{Elasticity} = \frac{\frac{F_{10}(2\text{ mm}) - F_{10}(1.5\text{ mm})}{0.5}}{\frac{F_1(2\text{ mm}) - F_1(1.5\text{ mm})}{0.5}} = \frac{E_{10}}{E_1}$$

(to calculate the elasticity, the deformation forces are determined for deformations of 1.5 mm and 2 mm respectively from the first and tenth cycles and ratioed).

EXAMPLES

Unless otherwise stated, the quantities are understood to be in weight percent.

1—Product—

The inventive styling agents A to F were manufactured as shown in the following Table.

| Raw materials | A | B | C | D | E | F |
|---|---|---|---|---|---|---|
| 2-Amino-2-methylpropanol, 95% | 0.37 | 1.11 | 0.07 | 0.17 | 0.66 | 0.66 |
| Luviquat Ultra Care [1] | 19.23 | 19.23 | — | — | — | — |
| Luviquat Hold [2] | — | — | 12.50 | 2.50 | 2.50 | — |
| Luviquat Supreme [3] | — | — | — | — | — | 2.50 |
| Luviflex Soft [4] | — | 8.15 | — | — | — | — |
| Fixate G-100 [5] | 9.55 | — | — | — | — | — |
| Fixomer A-30 [6] | — | — | 20.81 | — | — | — |
| Aculyn 28 [7] | — | — | — | 2.52 | — | — |
| Synthalen K [8] | — | — | — | — | 0.71 | 0.71 |
| Water, deionized | ad 100 | ad 100 | ad 100 | ad 100 | ad 100 | ad 100 |

[1] Copolymer of vinyl pyrrolidone and N-methyl vinyl imidazole (ca. 13 wt. % solids in water; INCI name: Polyquaternium-44) (BASF)
[2] Copolymer of vinyl caprolactam, vinyl pyrrolidone and N-methyl vinyl imidazole (ca. 20 wt. % solids in water; INCI name: Polyquaternium-46) (BASF)
[3] Copolymer of vinyl pyrrolidone, methacrylamide, vinyl imidazole and N-methyl vinyl imidazole (ca. 20 wt. % solids in water; INCI name: Polyquaternium-68) (BASF)
[4] Copolymer of ethyl acrylate and methacrylic acid, 30% dispersion in water (INCI name: Acrylates Copolymer) (BASF)
[5] Copolymer of acrylic acid and allyl methacrylate, partially neutralized with aminomethylpropanol (ca. 27 wt. % solids in water; INCI name: AMP Acrylates/Allyl Methacrylate Copolymer) (Noveon)
[6] Copolymer of methacrylic acid and acrylamidomethyl propane sulfonic acid (10.5-13.1 wt. % solids in water; INCI name: Methacrylic Acid/Sodium Acrylamidomethyl Propane Sulfonate Copolymer) (Nalco)
[7] Copolymer of one or more monomers of acrylic acid, methacrylic acid and their simple esters (ca. 20 wt. % solids in water; INCI name: Acrylates/Beheneth-25 Methacrylate Copolymer) (Rohm&Haas)
[8] Polyacrylic acid (solid); INCI name: Carbomer (3V Sigma)

2—Proof of Effectiveness—

The hold, the flexibility, the elasticity and the plasticity obtained by applying various polymers on human hair were determined by the Omega-Loop method (50 resp. 75% relative humidity, 25° C.).

The inventive styling agents A to F comprise the polymers (based on pure polymer) in amounts of either 5 wt. % (A, B, C) or in amounts of 1 wt. % (D, E, F).

Accordingly, non-inventive styling agents a1 to f1 and a2 to f2, shown in the following Tables, were then manufactured as comparative formulations—

| Raw materials | a1 | b1 | c1 | d1 | e1 | f1 |
|---|---|---|---|---|---|---|
| 2-Amino-2-methylpropanol, 95% | 0.73 | 2.21 | 0.12 | 0.34 | 1.32 | 1.32 |
| Luviquat Ultra Care [1] | — | — | — | — | — | — |
| Luviquat Hold [2] | — | — | — | — | — | — |
| Luviquat Supreme [3] | — | — | — | — | — | — |
| Luviflex Soft [4] | — | 16.30 | — | — | — | — |
| Fixate G-100 [5] | 19.09 | — | — | — | — | — |
| Fixomer A-30 [6] | — | — | 41.62 | — | — | — |
| Aculyn 28 [7] | — | — | — | 5.03 | — | — |
| Synthalen K [8] | — | — | — | — | 1.42 | 1.42 |
| Water, deionized | ad 100 | ad 100 | ad 100 | ad 100 | ad 100 | ad 100 |

-continued

| Raw materials | a2 | b2 | c2 | d2 | e2 | f2 |
|---|---|---|---|---|---|---|
| 2-Amino-2-methylpropanol, 95% | 0.01 | 0.01 | 0.01 | 0.002 | 0.002 | — |
| Luviquat Ultra Care [1] | 38.46 | 38.46 | — | — | — | — |
| Luviquat Hold [2] | — | — | 25.00 | 5.00 | 5.00 | — |
| Luviquat Supreme [3] | — | — | — | — | — | 5.00 |
| Luviflex Soft [4] | — | — | — | — | — | — |
| Fixate G-100 [5] | — | — | — | — | — | — |
| Fixomer A-30 [6] | — | — | — | — | — | — |
| Aculyn 28 [7] | — | — | — | — | — | — |
| Synthalen K [8] | — | — | — | — | — | — |
| Water, deionized | ad 100 | ad 100 | ad 100 | ad 100 | ad 100 | ad 100 |

These each comprised only one polymer that was added in equal amounts of active substance (5 wt. % resp. 1 wt. %).

The comparative examples a1 to f1 and a2 to f2 were tested with the omega-loop method. The resulting values were used as the base line for the calculation of an expected value for combinations of two polymers. For example, if the formulation a1 results in a value of 3 and the formulation a2 a value of 1, then the expected value for the corresponding 1:1 mixture (inventive gel A) is (3+1)/2=2.

The polymer mixtures were then measured with the omega loop method at 50% relative humidity and 75% relative humidity and the deviation from the expected value was measured. The moisture stabilities can be determined from the ratios of the values at 75% relative humidity to the values at 50% relative humidity. The obtained results are presented in the following table—

|   | Hold [N] | Flexibility | Elasticity | Plasticity |
|---|---|---|---|---|
| A | >10% better | equal | >20% better | >20% better |
| B | >10% better | >20% better | >20% better | equal |
| C | >10% better | >20% better | >20% better | >20% better |
| D | >10% better | >20% better | equal | >20% better |
| E | >10% better | equal | equal | >20% better |
| F | >10% better | >20% better | >20% better | >20% better |

The results show that the polymer combinations show significantly better results in comparison to the expected values and in this regard exhibit significantly improved degrees of hold both for experiments carried out at 50% relative humidity and at 75% relative humidity, wherein flexibility, elasticity and plasticity are comparable or even better. The polymer combinations according to the invention thereby show unexpected synergistic effects.

We claim:

1. Cosmetic agent comprising, in a cosmetically acceptable carrier:
   a) at least one copolymer A having
      at least one structural unit according to Formula (I)

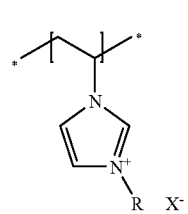

(I)

wherein R is a $C_1$ to $C_{30}$ alkyl group, a $C_1$ to $C_4$ aralkyl group, a $C_2$ to $C_6$ alkenyl group or a $C_2$ to $C_6$ hydroxyalkyl group; and $X^-$ is a physiologically compatible anion, and at least one further structural unit according to Formula (II)

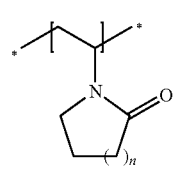

(II)

wherein n is 1, 2 or 3 as the number of methylene units; and b) at least one acrylate polymer B different from copolymer A and chosen from copolymers of methacrylic acid with acrylamido propane sulfonic acid,
   wherein the total quantity of polymer B, based on total weight of the agent, is from 0.05 wt. % to 5.0 wt. % of the cosmetic agent, and wherein the weight ratio of polymer(s) A to polymer(s) B is from 4:1 to 1:4.

2. Agent according to claim 1 comprising a copolymer A1 as copolymer A, said copolymer A1 comprising
   at least one structural unit according to Formula (I)

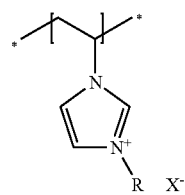

(I)

wherein R is a methyl group and $X^-$ is methosulfate, and
   at least one further structural unit according to Formula (II)

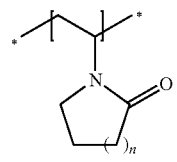

(II)

wherein n is 1 methylene unit.

3. Agent according to claim 2 wherein copolymer A1 comprises 10 to 30 mol% of structural units according to Formula (I) and 70 to 90 mol% of structural units in accordance with Formula (II).

4. Agent according to claim 2 wherein the molar mass of copolymer A1 is from 50 to 400 kDa.

5. Agent according to claim 1 comprising a copolymer A2 as copolymer A, said copolymer A2 comprising at least one structural unit according to formula (I)

(I)

wherein R is a methyl group and X⁻ is methosulfate, at least one further structural unit according to Formula (II)

(II)

wherein n is 1 methylene unit, and at least one further structural unit according to Formula (II)

(II)

wherein n is 3 methylene units.

6. Agent according to claim 5 wherein copolymer A2 comprises 1 to 20 mol% of structural units in accordance with Formula (I), 30 to 50 mol% of structural units according to Formula (II) with n =1, and 40 to 60 mol% of structural units according to Formula (II) with n =3.

7. Agent according to claim 5 wherein the molar mass of copolymer A2 is from 100 to 1000 kDa.

8. Agent according to claim 1 comprising a copolymer A3 as copolymer A, said copolymer A3 comprising at least one structural unit according to formula (I)

(I)

wherein R is a methyl group and X is methosulfate, at least one further structural unit according to Formula (II)

(II)

wherein n is 1 methylene unit, at least one further structural unit according to Formula (III)

(III)

and at least one further structural unit according to Formula (IV)

(IV)

9. Agent according to claim 8 wherein the copolymer A3 comprises 1 to 12 mol% of structural units according to Formula (I) and 45 to 65 mol% of structural units according to Formula (II) with n =1, 1 to 20 mol% of structural units according to Formula (III), and 20 to 40 mol% of structural units according to Formula (IV).

10. Agent according to claim 8 wherein the molar mass of copolymer A3 is from 100 to 500 kDa.

11. Agent according to claim 1 wherein the total quantity of copolymer A, based on total weight of the agent, is 0.05 to 5 wt.%.

* * * * *